United States Patent [19]
Thomas et al.

[11] Patent Number: 5,824,865
[45] Date of Patent: Oct. 20, 1998

[54] CHIMERIC PLANT GENES BASED ON UPSTREAM REGULATORY ELEMENTS OF HELIANTHININ

[75] Inventors: Terry Thomas, College Station, Tex.; Georges Freyssinet, Saint Cyr au Mont d'Or, France; Michel Lebrun, Lyon, France; Molly Bogue, Strasbourg, France

[73] Assignee: Rhone Poulenc Agrochimie, Lyon Cedex, France

[21] Appl. No.: 480,346

[22] Filed: Jun. 7, 1995

Related U.S. Application Data

[62] Division of Ser. No. 243,541, May 16, 1994, which is a continuation of Ser. No. 116,041, Sep. 1, 1993, abandoned, which is a continuation of Ser. No. 682,354, Apr. 8, 1991, abandoned.

[51] Int. Cl.$^6$ .......................... C12N 15/29; C12N 15/82; C12N 5/04; A01H 5/00
[52] U.S. Cl. ................................. 800/205; 800/DIG. 14; 800/DIG. 17; 800/DIG. 26; 800/DIG. 27; 800/DIG. 43; 800/DIG. 56; 435/320.1; 435/172.3; 435/240.4; 536/23.6; 536/24.1
[58] Field of Search ........................... 800/205, DIG. 14, 800/DIG. 17, DIG. 26, DIG. 27, DIG. 43, DIG. 56; 435/320.1, 172.3, 240.4; 536/23.6, 24.1

[56] References Cited

FOREIGN PATENT DOCUMENTS

WO91/13972  9/1991  WIPO ............................ C12N 15/00

OTHER PUBLICATIONS

Bogue et al. (1990) "Developmentally regulated expression of a sunflower 11S seed protein gene in transgenic tobacco" *Molecular and General Genetics* 222:49–57.

Thomas et al. (1991) "ABA regulation of gene expression in embryos and mature plants" In: *Abscisic Acid: Psychology and Biochemistry*, (Ed. by Davis and Jones) 125–136.

Thomas et al. (1991) "ABA regulation of two distinct plant embryo genes" *J. Cell Biochem. (Suppl)*, 18A:126.

Thomas et al. (1991) "ABA regulation of gene expression in embryos and mature plants" *J. Exp. Bot.*, 42:10.

Bustos et al. (1989) *Plant Cell I*, 839–853.

Chen et al. (1988) *Embo Journal* 7, 297–302.

Colot et al. (1987) *Embo Journal* 6, 3559–3564.

Goldberg et al. (1989) *Cell* 56, 149–160.

Jordano et al. (1989) *Plant Cell I*, 855–866.

Marris et al. (1988) *Plant Molecular Biology* 10, 359–366.

Schernthaner et al. (1988) *Embo Journal* 7, 1249–1255.

Vonder Harr et al. (1988) *Gene* 74, 433–443.

Wada et al., *Nature*, 347: 200–203 (1990).

*Primary Examiner*—David T. Fox
*Assistant Examiner*—Melissa L. Kimball
*Attorney, Agent, or Firm*—Scully, Scott, Murphy & Presser

[57] ABSTRACT

Helianthinin is an 11S seed storage protein of sunflower embryos. The present invention is directed to the 5' regulatory regions of helianthinin genes. More particularly, the present invention is directed to specific cis-regulatory elements of this regulatory region which direct abscisic acid-responsive gene expression. The present invention provides chimeric genes comprising the cis-regulatory elements linked to a coding sequence from a heterologous gene to control expression of these genes. The chimeric genes provided by the instant invention are useful in conferring herbicide resistance and improved seed lipid quality to transgenic plants.

39 Claims, 12 Drawing Sheets
(1 of 12 Drawing(s) Filed in Color)

```
                -60   |   -50    |   -40    |
-2377                                       GGATCCT
-2340 TTTAAAAAAA TCCCGTACCC CTCGAAAAA
-2280 CCTAAAGAGC CGCCCATGCT TTTTAATCAA
-2220 ACTAAAATCC ATTAGTTTAT AAATATTTTA
-2160 AAATTAAAAA ACAAAATGTC CAAAATACTC
-2100 CCCTTTTGGT TAACAAAGTC TTTAATTTAA
-2040 AAAAACGAAC GTGGGGCGC GGGGGTGGGG
-1980 TTAAAGTATA AAAATTGCCC AAACCTCAGG
-1920 AATACTAAAA TACACCAAGT CAATGGGTGA
-1860 ATTACCTTAT TTACTTTTGA GAAAGACGAC
-1800 TTTGCGCTAT TTTTCATACT TAAGGTCCAG
-1740 TTGATCATAA CAATATAACA ATTAAGGAGT
-1680 TACTAATTAA GGTCCGGTT TGAATCTCTC
-1620 ATGAGACATG CTCACAATGG GAATTGAACC
-1560 ACAAACTGAG CTACACATTT TTAATTTAAA
-1500 TTTATTTTGA TTTGTTTTGT TAATGTATTT
-1440 ATAATATTAG TAATATTTTA TTAACATCAA
-1380 TTTTTTATAT GGTTTTATCA GTGGTGTGGT
-1320 ACTTCTTGGT TGTTACTTAT TGATGTACGA
-1260 AATAACATTT TGGATAAGAT TACGACTTTA
-1200 TGGGTTAAGA CACAACCACA TATAATGTGA
-1140 CTTTTGTTAC AAATGTTGTT AACTAGGCTT
-1080 GTTCTTACGG TTTTACATCT AGTAAGAGAT
-1020 AAAGAGAGTA AAGAGAATGT AGCCATGATA
 -960 ACTTATCATC TTGATGATGC ATATAGACAT
 -900 TTCCCGGCGC AACACACGTG TATAAATACC
 -840 GGTGGTTATA TGATACCTAT GATGACTTGA
 -780 AAAAAATGTG GCTATAGGCG CATGGTCACA
 -720 ACGTAGCGTT AGTTAATCAG ATAAATTTAT
 -660 TAATTTCAAG TAGACGTGTA TTTATATAAT
 -600 GCTTCATGTT TTGGGTTAGT CTTCGTTTTT
 -540 GATTATTTAA ATAATGACGG ACTTCTTGGT
 -480 TAACGAACCG AACACATATA AATAACATTT
 -420 GCCATGAAAT TTGGAAGACT TGGGTTAAGA
 -360 CATTTACAAC TAATGTTAAT CTTTTGTTAC
 -300 ATTTTAAAG ACTATATGGT GTTCTTACGG
 -240 AAAAAAGCA AGGAAAGTAA GTGTAAAGAG
 -180 ATTGTTCATC ACCATCCCAT TTATACTTAT
 -120 TACTTATACA GATGTAGCAT GTCTCAGCTC
  -60 TTAGATGTCA CTTCCTCCTT GATCTTCTTC
    1 ATTCACCACA TCACATCCCA TTCC
              |   10    |   20    |    30
```

FIG. 1-1

```
            -30      |   -20      |  -10       |
         CTACCTATAT ATATATATAT ATATGAATTT  -2341
         CGGGCCTTAT GCGGAAGTCC TCCTCGCACA  -2281
         ATAGATGTGC ATCATGTAGT GATAGTTTTT  -2221
         AATGTTTTTT TTTGTTTATA TAAAAAAGA   -2161
         CTGTATCAAC TATGCAAAAA GACAAAAAA   -2101
         CTAAGTTTGT CATTTGAAGG AAATTCAAAC  -2041
         TGTTTGGTTA CAAAAAGTTT TAATTTTAGA  -1981
         ACAATTTTTA CATTTATAAC TCATTGTCTA  -1921
         AAGTTACTAT CTTTTTTATT GCAATTTCAC  -1861
         ATAACAATTA AGGAGTTATA GTCTGATCGG  -1801
         GTTTGAATCT TTTAAACATT TTTTTTTAAC  -1741
         TATGATCTGA TGGTTTGCGT TATGTTTTCG  -1681
         AAACAATATA TTATTTTTC TTAAAACGA    -1621
         GACACCTATT GGTTAAAAT TAAAGCTATA   -1561
         AATGTCGACT ATCTTAGTTA ATCAAATAAA  -1501
         TCTCCTAATT TAAAGTCGAT GTGTATTTAT  -1441
         TACATGCTTC AGGTTTTGTG TTAGTCTTCG  -1381
         GTACGATGAC GATTATTTAA ATAATGACGA  -1321
         AGCTGAGATG TAACGAACCG AACACATATA  -1261
         TTTATCGGTT GCCATGAAAT TTAGAAGATT  -1201
         TGGTAAATAG CATTTACAAC TAATGTTAAT  -1141
         GATATGTAAA ATTTTTAAAG ACTATCAGGT  -1081
         TAAAAAAAA AAAGCAAGGA AAGTAAGTGT   -1021
         TGGCTGATTG TTCATCACCA TCCCATTTAT  -961
         GATGTGTGCT ACGTACCGAA TTTTAACAGC   -901
         ATAGATTATA AACCAAATAC GCTACGTATA   -841
         CCTTTCGTTA CACTTGAGCT GAAAAAATA    -781
         GTTTTTTTGT GTGGCCATAT ACAATTTTTG   -721
         TTTGATTTGT TTTGTTAATG TATTTCTCC    -661
         ATTAGTAATA TTTTATTAAC ATCAATACAT   -601
         TATATGGTTT TATCAGTGGT GTACGATGAC   -541
         TGTTACTTAT TGATGTACGA AGCTGAGATG   -481
         TGGATAAGAT TACGACTTTA TTTATCGGTT   -421
         CACAACCACA TATAATGTGA TGGTAAATAG   -361
         AAATGTTGTT AACTAGGCTT GATATGTAAA   -301
         TTTTACATCT AGTAAGAGAT TAAAAAAAA    -241
         AGTAAAGAGA ATGTAGCCAT GATATGGCTG   -181
         CATCTTGATG ATGCATATAG ACAACACAC    -121
         CAAATGGTGA TCTTCTCCTG GCATAACCTC   -61
         CACTATAAAA CCAGCTAGTT CACAACACCT   -1
                                            24
            |   40     |   50     |  60
```

FIG. I-2

```
         -60    |    -50    |    -40    |
-2457        GGATCCT  GTAAGAAGTG  CCCAAAATGT
-2400  CTATATAACA  CCATATAAAT  ACCGTATAAC
-2340  GCTATGTAAC  ACTATATAAC  ATTATATAAC
-2280  ATGCTATCAG  ACAACCTATA  GTGTTATATT
-2220  CGTTATATGG  TATTATATGG  TGTTACATAT
-2160  TATTATATAT  AGTGTTATAA  TACACTTCTC
-2100  ACCTATATAT  ATATATATAT  ATATAAAGGA
-2040  GTGAACTGCG  TGAACTGATC  TCAGCCCTTG
-1980  GCATGATGGT  AATTATTTGG  TTAATTTTTT
-1920  GTGTAATTTC  AATCTTAAAT  TGATTGCATA
-1860  TTCTTAAACT  GATTACATAA  ATCTCTCACA
-1800  TTAATTCTAA  TTACTAAAAT  AACTATTTGT
-1740  TTTTGCCCTC  TTTTTAATGT  GATGTACACA
-1680  AGAATTTTTT  TTGTATTGAA  TGTTGATGTA
-1620  ATGCTGATGC  TGAGTACACA  TGTGTACTGT
-1560  CTTGAAATAT  GAAAGTTACG  TGGATCTTAA
-1500  CTGAAATAAA  AATTAAAATT  GAAATCTGGT
-1440  TTAATAAATA  AACATAATGT  GGATAATGAA
-1380  ATTATTAAAA  TAATGATTTA  AATCTAATTT
-1320  CTAAAAGGA   AATCAAGGGT  TCATATCTGT
-1260  CGCTGGAACC  CTACCCTATA  TATATATATA
-1200  GTACCCCTCG  AAAAAACGGG  CCTTATGCGG
-1140  CATGCTTTTG  ATCAAATAGT  TGTAAATACT
-1080  CTATCTTTTT  TATTGCAATT  TCACATTACC
-1020  ATTAAGGAGT  TATAGTCTGA  TCGTTTGCGC
 -960  TATTTTAAAC  ATTTTTTTTA  ACTTGATCAT
 -900  GATGGTTTGC  GTTATGTTTT  CGTACTAATT
 -840  TATTATTTTT  ACCTAAAAAC  GAATGAGGCA
 -780  TTGGTTTAAA  ATTAAGCTA   TAACAAACTG
```

FIG. 2-1

```
          -30         |   -20        |    -10       |
        GAGAAGTGTA    TTATAACACT    ATATATAATA    -2401
        ACTATGTAAC    ACCATATAAC    ACAATATAAC    -2341
        AATATATAAC    ACTATACATC    TATCAGAGAC    -2281
        TGTTATATAA    TGTTATATAG    TGTTACATAG    -2221
        TGTTATACGT    GTTTATATGG    TGTTATATAG    -2161
        ACACTTTGGG    CACTTTTTAC    AGGATCATCT    -2101
        TTAGGTTCAA    ACGTGAACAA    ATTCCCAAGA    -2041
        ATTTTTATGA    TCTTGAGATT    AAAGTGAGTG    -1981
        TTCATTTAAT    TAAATACAAA    AAGGGTATAT    -1921
        AATCTCTCAC    AAATCAAGTA    ATCAATTATC    -1861
        AATCAAATCA    AGGATTAGGA    AAGATGTAAC    -1801
        TTAAATGCGA    TGTACACATG    TGTATTCTGA    -1741
        TGTGTATATC    GTCTGTTTTT    ATGAGATCTC    -1681
        CACCTGTGAA    TTACTGTACA    CATATGTACG    -1621
        TCTATTTATA    TCCAAGTACA    CATGTGTAAC    -1561
        AAATCAAAT     TTGAATTCTG    GTGATGAAAT    -1501
        GATTGTTGT     TTGTTTGAT     AATTATCTTA    -1441
        TTTAAATTAG    GAAAGATGTA    ACTTAATTCA    -1381
        TTTATATAAT    TACAATCCTA    CCCTTAACAA    -1321
        TCACGCAGTT    CACTCTTGGG    AGGTTGTTCA    -1261
        TATATATATC    AAATTTTTTT    AAAAAATCCC    -1201
        AAGTCCTCCT    CGCACACCTA    AAGAGCCGCC    -1141
        AAAATACACC    AAGTCAATGG    GTGAAAGTTA    -1081
        TTATTTACTT    TTGAGAAAGA    CGACATAACA    -1021
        TATTTTTCAT    ACTTAAGGTC    CAGGTTTGAA    -961
        AACAATATAA    CAATTAAGGA    GTTATGGTCT    -901
        AAGGTCCCGG    TTTGAATCTC    TCAAACAATA    -841
        TGCTCACAAT    GGGAATTGAA    CCGACACCTA    -781
        AGCTACACAT    TTTTAATTTA    AAAAT
```

FIG. 2-2

```
-720  CTATCTTAGT  TAATCAAATA  AATTTATTTT
-660  TTTAAAGTCG  ATGTGTATTT  ATATAATATT
-600  TCAGGTTTTG  TGTTAGTCTT  CGTTTTTTAT
-540  ACGATTATTT  AAATAATGAC  GGACTTCTTG
-480  TGTAACGAAC  CGAACACATA  TAAATAACAT
-420  TTGCCATGAA  ATTTGGAAGA  CTTGGGTTAA
-360  AGCATTTACA  ACTAATGTTA  ATCTTTTGTT
```

FIG. 3-1

```
                              GTCGA -721
GATTTGTTTT  GTTAATGTAT  TTTCTCCTAG -661
AGTAATATTT  TATTAACATC  AATACATGCT -601
ATGGTTTTAT  CAGCGGTGTG  GTGTACGATG -541
GTTGTTACTT  ATTGATGTAC  GAAGCTGAGA -481
TTTGGATAAG  ATTACGACTT  TATTTATCGG -421
GACACAACCA  CATATAATGT  GATGGTAAAT -361
ACAAATGTT
```

FIG. 3-2

CHIMERIC PLANT GENES BASED ON UPSTREAM REGULATORY ELEMENTS OF HELIANTHININ

This is a divisional of application Ser. No. 08/243,541, filed May 16, 1994, which is a continuation of Ser. No. 08/116,041, filed Sep. 1, 1993, now abandoned, which is a continuation of Ser. No. 07/682,354, filed Apr. 8, 1991, now abandoned.

FIELD OF THE INTENTION

Helianthinin is an 11S seed storage protein of sunflower embryos. The present invention is directed to the 5' regulatory regions of helianthinin genes. More particularly, the present invention is directed to specific cis-regulatory elements of this regulatory region which direct tissue-specific, temporally-regulated, or abscisic acid-responsive gene expression. The present invention provides chimeric genes comprising the cis-regulatory elements linked to a coding sequence from a heterologous gene to control expression of these genes. The chimeric genes provided by the instant invention are useful in conferring herbicide resistance and improved seed lipid quality to transgenic plants.

BACKGROUND OF THE INVENTION

Seed development, unique to higher plants, involves embryo development as well as physiological adaptation processes that occur within the seed to ensure the survival of the developing seedling upon germination. After fertilization, there is rapid growth and differentiation of the embryo and endosperm, after which nutritive reserves accumulate during the maturation stage of seed development. These reserves are stored during a period of developmental arrest for later use by the developing seedling. This period of arrest occurs prior to the desiccation phase of seed development.

Several classes of seed proteins, including storage proteins, lectins, and trypsin inhibitors, accumulate during embryogenesis. The main function of seed storage proteins is to accumulate during embryogenesis and to store carbon and nitrogen reserves for the developing seedling upon germination. These proteins, as well as many of the genes encoding them, have been studied extensively (for review see Shotwell et al. (1989) in *The Biochemistry of Plants*, 15, Academic Press, NY, 297).

Genes encoding seed storage proteins are highly regulated and differentially expressed during seed development. Expression is temporally regulated with MRNA accumulating rapidly during the maturation phase of embryogenesis. This expression is also tissue-specific, occurring primarily in the cotyledons or endosperm of the developing seeds. The resulting storage proteins are processed and targeted to protein bodies, in which the storage proteins remain during desiccation and dormancy of the embryo. Upon germination, the seedling uses these storage proteins as a source of carbon and nitrogen (Higgins (1984) *Ann. Rev. Plant Physiol.* 35, 191).

Seed proteins, including storage proteins, lectins and trypsin inhibitors, are encoded by nonhomologous multigene families that are not amplified or structurally altered during development (for review see Goldberg et al. (1989) *Cell* 56, 149). These genes are temporally and spatially regulated but not necessarily linked. Although post-transcriptional mechanisms act to control the accumulation of some of these proteins, regulation occurs primarily at the transcriptional level. Accordingly, seed protein genes provide an excellent system to provide genetic regulatory elements, especially those elements which confer tissue specificity, temporal regulation, and responsiveness to environmental and chemical cues.

Observations of temporal and spatial regulation of seed protein genes has suggested that seed protein genes are regulated in part by common cellular factors known as trans-acting factors. However, since quantitative and qualitative differences exist in the expression patterns of individual seed protein genes, more specific factors must also exist to provide a means for differential expression patterns between these groups of seed proteins. Patterns of differential expression have been observed between the rapeseed major seed storage proteins, cruciferin and napili (Crouch et al. (1981) *Planta* 153, 64; Finkelstein et al. (1985) *Plant Physiol.* 78, 630), and among individual members of the soybean Kunitz trypsin inhibitor gene family (Jofuku et al. (1989) *Plant Cell* 1, 1079). A comparison of the soybean major seed storage protein genes showed a difference in timing and cell-type specificity of the expression of B-conglycinin (7S) and glycinin (11S). The 7S subunit mRNA appeared several days before the 11S MRNA. Furthermore, while members of the glycinin gene family were all activated simultaneously (Nielsen et al. (1989) *Plant Cell* 1, 313), members of the β-conglycinin gene family were differentially regulated (Barker et al. (1988) *Proc. Natl. Acad. Sci. USA* 85, 458; Chen et al. (1989) *Dev. Genet.* 10, 112). Each of these genes contain a different array of cis-regulatory elements which confer differential expression patterns between, and within, these gene families.

Helianthinin is the major 11S globulin seed storage protein of sunflower (*Helianthus annuus*). Helianthinin expression, like that of other seed storage proteins, is tissue-specific and under developmental control. However, the helianthin regulatory elements which confer such specificity have heretofore never been identified. Helianthinin MRNA is first detected in embryos 7 days post flowering (DPF) with maximum levels of MRNA reached at 12–15 DPF, after which the level of helianthinin transcripts begins to decline. In mature seeds or in germinating seedlings helianthinin transcripts are absent. Helianthinin polypeptide accumulation is rapid from 7 DPF through 19 DPF but slows as the seed reaches later maturation stages (Allen et al. (1985) *Plant Mol. Biol.* 5, 165).

Helianthinin, like most seed proteins, is encoded by a small gene family. At least two divergent subfamilies are known, and are designated Ha2 and Ha10. Two clones, HaG3-A and Ha-3-D, representing non-allelic members orf the Ha2 subfamily, have been isolated and partially characterized (Vonder Haar et al. (1988) *Gene* 74, 433). However, a detailed analysis of the regulatory elements of these or any other helianthinin genes had not been known until now.

It has been found in accordance with the present invention that regulatory elements from helianthinin genes can direct seed-specific gene expression, root-specific gene expression, abscisic acid-responsive gene expression, and/or temporally-altered gene expression. These regulatory elements enable the controlled expression of specific gene products in transgenic plants. The present invention provides greater control of gene expression in transgenic plants, thus allowing improved seed quality, improved tolerance to environmental conditions such as drought, and better control of herbicide resistance genes.

SUMMARY OF THE INVENTION

The present invention is directed to the 5' regulatory region of a helianthinin gene. This region is herein referred to as the upstream regulatory ensemble (URE), and is useful in directing the expression of heterologous proteins. The URE consists of multiple regulatory elements which confer distinct regulated expression patterns when linked to the coding regions of heterologous genes which are expressed in transgenic plants.

In particular, the present invention provides isolated DNA containing helianthinin regulatory elements which direct seed-specific gene expression, root-specific gene expression, abscisic acid (ABA)-responsive gene expression and/or temporally-altered gene expression.

Another aspect of this invention is directed to chimeric plant genes containing these regulatory elements. The regulatory elements are operably linked to the coding sequence of a heterologous gene such that the regulatory element is capable of controlling expression of the product encoded by the heterologous gene. If necessary, additional promoter elements or parts of these elements are included in the chimeric gene constructs. Plant transformation vectors comprising the chimeric genes of the present invention are also provided, as are plant cells transformed by these vectors, and plants and their progeny containing the chimeric genes.

In yet another aspect of this invention, a method is provided for producing a plant with improved seed-lipid quality. Chimeric genes are constructed according to the present invention in which a regulatory element directing seed-specifics expression is linked to the coding region of a gene encoding a lipid metabolism enzyme. When plant cells are transformed with this chimeric gene, plants with improved seed lipid-quality can be regenerated.

A further aspect of the present invention provides a method for producing a herbicide-resistant plant. In accordance with the present invention, for example, chimeric genes are constructed in which a root-specific regulatory element directs the expression of herbicide-resistance gene. Plant cells are transformed with this chimeric gene to regenerate herbicide-resistant plants.

BRIEF DESCRIPTION OF THE DRAWINGS

The file of this patent contains at least one drawing executed in color. Copies of this patent with the color drawing will be provided by the U.S. Patent and Trademark Office upon request and payment of the necessary fee.

FIG. 1 depicts the nucleotide sequence of the URE of helianthinin gene HaG3-A. Nucleotide numbers −2377 to +24 of FIG. 1 correspond to nucleotide numbers 1 to 2401 of SEQ ID NO:1.

FIG. 2 aspects the nucleotide sequence of part of the URE of helianthinin gene HaG3-D. Nucleotide numbers −2457 to −726 of FIG. 2 correspond to nucleotide numbers 1 to 1732 of SEQ ID NO:2.

FIG. 3 represents the nucleotide sequence of part or the URE of helianthinin gene HaG3-D. Nucleotide numbers −725 to −322 of FIG. 3 correspond to nucleotide numbers 1 to 404 of SEQ ID NO:3. In the helianthinin gene HaG3-D, the nucleotide sequence of FIG. 3 is immediately downstream (3') of the sequence of FIG. 2.

DETAILED DESCRIPTION OF THE INVENTION

Figure 4:
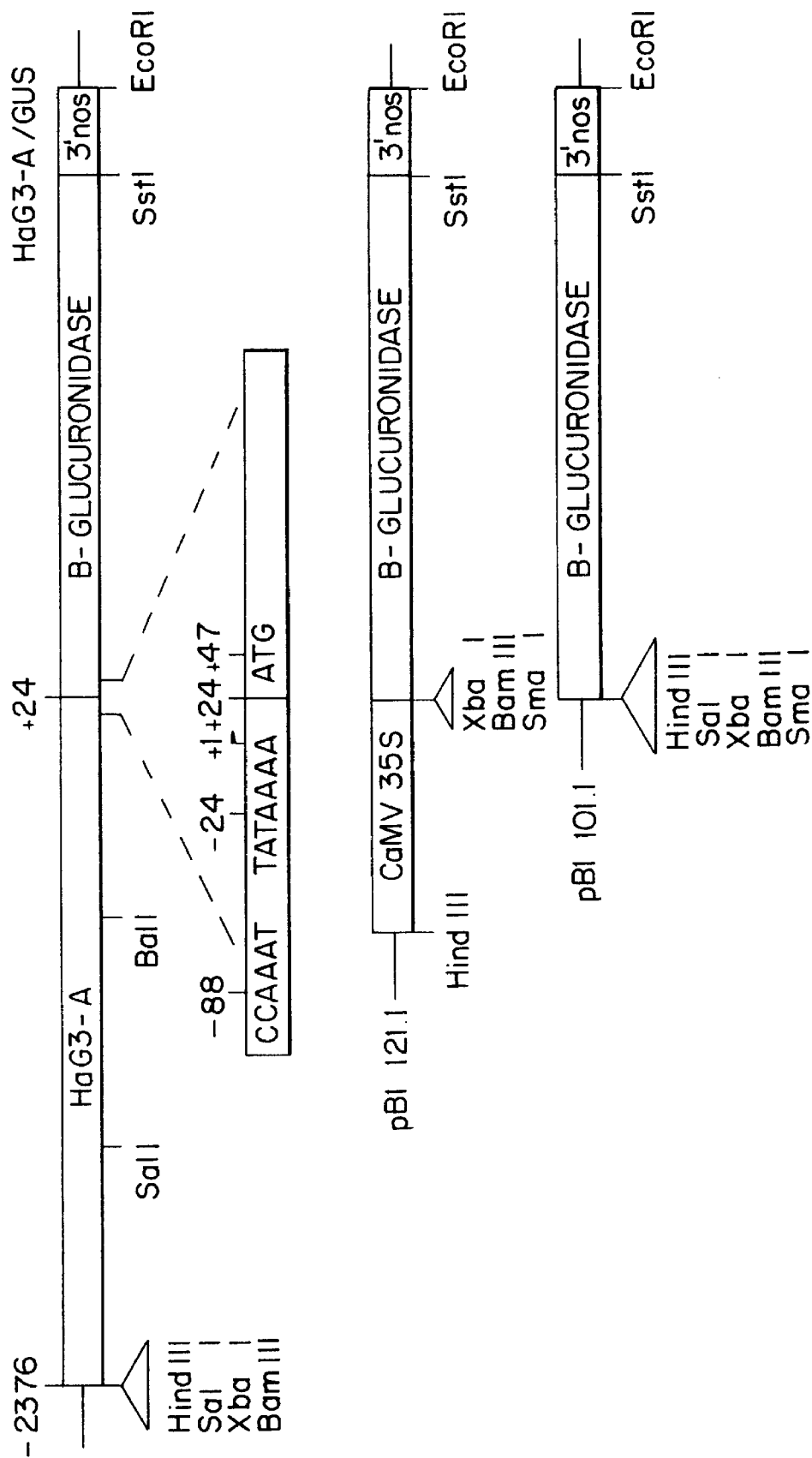
FIG. 4 depicts the HaG3-A FLIGUS construction and the control constructions pBI121.1 and pBI101.1.

The present invention comprises cis-regulatory elements of the upstream regulatory ensemble (URE) of sunflower helianthinin genes. These cis-regulatory elements are discrete regions of the URE that confer regulated expression upon the gene under their control. In particular, this invention Provides isolated nucleic acid containing at least one regulatory element from a helianthinin gene which directs at least one of the following: seed-specific gene expression, root-specific gene expression, ABA-responsive gene expression or temporally-altered gene expression. Any helianthinin gene can provide the regulatory elements, including Ha2 and Ha10 genes, which represent two divergent helianthinin gene subfamilies. In a preferred embodiment, the helianthinin genes are HaG3-A and HaG3-D, which are members of the Ha2 subfamily.

One of the subject regulatory elements directs seed-specific expression. A seed-specific regulatory element represents a particular nucleotide sequence that is capable of causing the expression of the gene under its control to occur in the seed, i.e. for the gene produced to be detected in the seed. Expression that is seed-specific may be in any part of the seed, e.g., but not limited to, the cotyledons and embryonic axis of the embryo and to the endosperm. No gene expression is detected in seedlings or somatic tissues of the adult plant for genes under seed-specific control.

To identify regulatory elements that direct seed-specific expression, a deletion analysis of the entire URE of a helianthinin gene can be performed. In a deletion analysis, nucleotides are successively removed from the entire URN, and the resulting fragments are ligated to the coding sequence of a reporter gene or other heterologous gene. The constructs are then analyzed for their ability to direct seed-specific expression by detecting the presence of the reporter gene product in seed tissues and not in other tissues. The seed-specific elements which have been identified can also be modified, e.g. by site-directed mutagenesis. The modified regulatory elements can then be assayed for their ability to direct seed-specific expression, thereby identifying alternative sequences that confer seed-specificity. These techniques for identifying regulatory elements are applicable to all helianthinin genes. For example, in a preferred embodiment an analysis of the URE of the helianthinin HaG3-A gene indicates that seed-specific regulatory elements are provided by nucleotides 851 to 2401, and by nucleotides 1 to 2401 of SEQ ID NO:1.

Other regulatory elements provided by the present invention provide root-specific expression. Root-specific expression is of particular interest and importance. Normally the sunflower helianthinin gene is expressed only in seeds. When particular regions of the helianthinin URE are isolated from the entire URE in accordance with the present invention, expression is exclusively localized to plant roots. A root-specific regulatory element represents a particular nucleotide sequence that is capable of causing the expression of the gene under its control to occur in plant roots and not in other plant tissues. Regulatory elements that direct root-specific expression are identified by analyzing fragments of a helianthinin URE for their ability to confer root-specific expression as described above for the identification of seed-specific regulatory elements except expression is detected in root tissues. Modifications of the nucleotide sequences that permit root-specific expression are also identified as described above. Root-specific regulatory elements from any helianthinin gene can be identified by such techniques. For example, in a preferred embodiment, an analysis of the URE of the helianthinin HaG3-A gene indicates that nucleotides 1 to 1639 and nucleotides 851 to 1639 of SEQ ID NC:1 represent root-specific regulatory elements.

Helianthinin expression is under strict temporal control, with mPNA first detected at 12 DPF. Accordingly, it has been discovered that cis-regulatory elements exist which confer temporally-altered gene expression which is detectable as early as about 4 DPF.

To identify regulatory elements that confer temporally-altered gene expression, a deletion analysis of the entire URE of a helianthinin gene can be performed. Fragments of the URE are linked to the coding sequence of a heterologous gene and the resulting chimeric construction is used to transform plants. Seeds from transformed plants are staged by days post flowering, and the staged seeds are assayed to detect the expression of the heterologous gene. Elements that direct expression of the heterologous gene before about 10 DPF are identified as elements that confer temporally-altered expression. Modifications of the nucleotide sequences of such elements that confer the desired phenotype can be identified as described above. These techniques for identification of regulatory elements that confer temporally-altered gene expression are applicable to all helianthinin genes. In a preferred embodiment, an analysis of the URE of the helianthinin gene HaG3-A indicates that elements that confer temporally-altered gene expression are provided by nucleotide 1 to 851 and 1639 to 2303 of SEQ ID NO:1.

Another aspect of the present invention is directed to regions of the URE of helianthinin that confer abscisic acid (ABA)-responsive gene expression. An ABA-responsive element represents a particular nucleotide sequence that is capable of causing the gene under its control to be expressed in response to ABA. Expression of the gene under the control of the ABA-responsive element can be induced by treatment with ABA, or by external stimuli that are known to result in the initiation of ABA biosynthesis. For example, ABA biosynthesis is initiated as a result of loss of turgor caused by environmental stresses including water-deficit, water-stress and salt-stress (reviewed in Zeevaart et al. (1988) *Annu. Rev. Plant Physiol.* 39, 439). Levels of ABA also increase in response to wounding, (Peña-Cortes et al. (1989) *Proc. Natl. Acad Sci. USA* 86, 9351). ABA-responsive elements are identified as described above for the identification of other regulatory elements. For example, deletion analysis can be used to identify nucleotide sequences of any helianthinin gene that induce the expression of a gene under its control in response to ABA. Such sequences can be modified as described above, and assayed to identify alternative sequences that confer ABA-responsive expression. In one preferred embodiment, an analysis of the URE of the helianthinin HaG3-A gene indicates that nucleotides 1 to 2401 of SEQ ID NO:1 provide an element that confers ABA-responsive expression in seeds. In another preferred embodiment, nucleotides 851 to 1639 or 1639 to 2303 of SEQ ID NO:1 provide an element that confers ABA-responsive expression in leaves of adult plants. In yet another preferred embodiment, an analysis of the URE of the helianthinin HaG3-D gene indicates that nucleotides 1 to 404 of SEQ ID NO:3 confer ABA-responsive expression in non-embryonic tis;sues of plants.

Accordingly, ABA-responsive elements have utility in that specific environmental cues can initiate ABA biosynthesis, and further induce expression of genes under the control of an ABA-responsive element. Expression of heterologous genes driven by the ABA-responsive elements of the helianthinin URE is not restricted to seeds, but is also observed in leaves of adult plants and in tissues of seedlings.

An isolated nucleic acid encoding the upstream regulatory ensemble of a helianthinin gene can be provided as follows. Helianthinin recombinant genomic clones are isolated by screening a sunflower genomic DNA library with a CDNA recombinant representing helianthinin mRNA (Vonder Haar (1988) *Gene* 74, 433). Methods considered useful in obtaining helianthinin genomic recombinant DNA are contained in Sambrook et al., 1989, in *Molecular Cloning: A Laboratory Manual*, Cold Spring Harbor, NY, for example, or any of the myriad of laboratory manuals on recombinant DNA technology that are widely available. To determine nucleotide sequences, a multitude of techniques are available and known to the ordinarily skilled artisan. For example, restriction fragments containing a helianthinin URE can be subcloned into the polylinker site of a sequencing vector such as pBluescript (Stratagene). These pBluescript subclones can then be sequenced by the double-strand dideoxy method (Chen and Seeburg (1985) DNA 4, 165).

The nucleotide sequence for DNA encoding the URE of helianthinin gene clone HaG3A is shown in FIG. 1 and presented as SEQ ID NO:1. Similarly, the nucleotide sequence for DNA encoding a region of the URE of helianthinin clone HaG3D is shown in FIG. 2 and presented as nucleotide sequence SEQ ID NO:2. The UREs of other helianthinin genes can be obtained by the same strategy. Alternatively, clones representative of other members of the helianthinin gene family can he obtained by using the HaG3A or HaG3D coding or URE sequences of the present invention as hybridization probes to screen a helianthinin genomic library and identify the additional helianthinin genes.

The identification of cis-regulatory sequences that direct temporal, tissue-specific and ABA-responsive regulation can be accomplished by transcriptional fusions of specific sequences with the coding sequence of a heterologous gene, transfer of the chimeric gene into an appropriate host, and detection of the expression of the heterologous gene. The assay used to detect expression depends upon the nature of the heterologous sequence. For example, reporter genes, exemplifed by chloramphenicol acetyl transferase and β-glucuronidase (GUS), are commonly used to assess transcriptional and translational competence of chimeric constructions. Standard assays are available to sensitively detect the reporter enzyme in a transgenic organism. The β-glucoronidase (GUS) gene is useful as a reporter of promoter activity in transgenic tobacco plants because of the high stability of the enzyme in tobacco cells, the lack of intrinsic β-glucuronidase activity in higher plants and availability of a qualitative fluorimetric assay and a histochemical localization technique. Jefferson et al. [(987) *EMBO J,* 6. 3901)] have established standard procedures for biochemical and histochemical detection of GUS activity in plant tissues. Biochemical assays are performed by mixing plant tissue lysates with 4-methylumbelliferyl-β-D-glucuronide, a fluorimetric substrate for GUS, incubating one hour at 37° C., and then measuring the fluorescence of the resulting 4-methyl-umbelliferone. Histochemical localization for GUS activity is determined by incubating plant tissue samples in 5-bromo-4-chloro-3-indolyl-glucuronide (X-Gluc) for 18 hours at 37° C., and observing the staining pattern of X-Gluc. The construction of such chimeric genes allows definition of specific regulatory sequences required for regulation of expression, and demonstrates that these sequences can direct expression of heterologous genes in the manner under analysis.

Another aspect of the present invention is directed to a chimeric plant gene containing a regulatory element from a helianthinin gene which directs seed-specific gene expression, root-specific gene expression, ABA-responsive gene expression or temporally-altered gene expression linked to the coding sequence of a heterologous gene such that the regulatory element is capable of controlling expression of the product encoded by the heterologous gene. The heterologous gene can be any gene other than helianthinin. If necessary, additional promoter elements or parts of these elements sufficient to cause expression resulting in production of an effective amount of the polypeptide encoded by the heterologous gene are included in the chimeric constructs.

Accordingly, the present invention provides chimeric genes comprising regions of the helianthinin URE that confer seed-specific expression in accordance with this invention which are linked to a sequence encoding a lipid metabolism enzyme such as a desaturase. In a preferred embodiment, the regions of the URE comprise nucleotides 851 to 2401 or 1 to 2401 of HaG3-A as shown in SEQ ID NO:1. Any modification of these sequences which confers seed-specific expression is contemplated. Seeds accumulate and store proteins and lipids, both of significant agronomic importance. Because elements of the helianthinin URE can direct high, regulated expression in developing seeds, these elements have utility in improving seed lipid and/or protein quality. These elements are useful in regulating expression of genes encoding lipid metabolism enzymes, such as those involved in elongation and desaturation of fatty acids, and/or proteins, especially those with high lysine and methionine content. Chimeric genes containing these elements can be used to provide transgenic plant lines that accumulate and store significant amounts of specific classes of lipids and/or proteins.

In another aspect of the present invention chimeric genes are provided which have a region of the URE of helianthinin that confers root-specific expression fused to a heterologous gene. This construction confers expression spatially distinct from "normal" helianthinin expression in that the heterologous gene is expressed exclusively in plant roots. In other words, when a specific sequence is removed from the context of the entire URE, tissue-specific regulation is altered. In a preferred embodiment, the region of the HaG3-A URE comprises 1 to 1639 or 851 to 1639 of SEQ ID NO:1 and is fused in reverse orientation to the promoter although these elements function in either orientation. In another preferred embodiment the sequence providing herbicide resistance is at least part of the aroA gene. Any modification of these sequences which confers root-specific expression is contemplated.

Of particular importance is the use of these chimeric constructions to confer herbicide resistance. Since most herbicides do not distinguish between weeds and crop plants, the engineering of herbicide-resistant crop plants is of considerable agronomic importance in that it allows the use of broad-spectrum herbicides. Accordingly, the present invention provides chimeric genes comprising elements of a helianthinin URE that confer root-specific expression fused to at least part of a promoter that functions in plants and further fused to at least part of the aroA gene or a sequence encoding a polypeptide conferring herbicide resistance. Polypeptides that confer resistance to glyphosate and related inhibitors of 5-enolpyrovylshikimic acid-3-phosphate synthase (EPSP synthase), sulfonylureas, imidazolinones and inhibitors of acetolactase synthase (ALS) and acetohydroxy acid synthase (AHS) are contemplated. In a preferred embodiment the regions of the URE are 1 to 1639 or 851 to 1639 of HaG3-A, as shown in SEQ ID NO:1 and are fused in reverse orientation to the promoter. Any modification of these sequences which confers root-specific expression is contemplated.

In another aspect of the present invention chimeric genes are provided comprising elements of the URE of helianthinin that confer temporally-altered expression fused in forward or reverse orientation to at least part of a promoter that functions in plants and further linked to the coding region of a heterologous gene. In a preferred embodiment the elements of the URE are nucleotides 1 to 851 or 1639 to 2303 of HaG3-A, as shown in SEQ ID NO:1. Any modification of these sequences that confers temporally altered gene expression is contemplated.

Chimeric genes are provided comprising elements of the URE of a helianthinin that confer ABA-responsive expression optionally fused in forward or reverse orientation to at least part of a promoter that functions in plants further fused to a heterologous gene. In a preferred embodiment the element of the URE comprises 851 to 1639 or 1639 to 2303 of HaG3-A, as shown in SEQ ID NO:1, or nucleotides 1 to 404 of HaG3-D, as shown in SEQ ID NO:3. Of particular importance is the use of constructs that confer ABA-responsive expression to provide plants with improved tolerance to water stress.

The chimeric genes of the present invention are constructed by fusing a 5' flanking sequence of a helianthinin genomic DNA to the coding sequence of a heterologous gene. The juxtaposition of these sequences can be accomplished in a variety of ways. In a preferred embodiment the order of sequences, from 5' to 3', is a helianthinin upstream regulatory region, a promoter region, a coding sequence, and a polyadenylation site.

Standard techniques for construction of such chimeric genes are well known to those of ordinary skill in the art and can be found in references such as Saxbrook et al. (1989). A variety of strategies are available for ligating fragments of DNA, the choice of which depends on the nature of the termini of the DNA fragments. One of ordinary skill in the art recognizes that in order for the heterologous gene to be expressed, the construction requires promoter elements and signals for efficient polyadenylation of the transcript. Accordingly, the 5' helianthinin URE regions that contain the promoter sequences known as CAAT and TATA boxes can be fused directly to a promoterless heterologous coding sequence. Alternatively, the helianthinin URE regions that do not contain the CAAT and TATA boxes can be joined to a DNA fragment encoding a promoter that functions in plants. Plant promoters can be obtained commercially, or can be chemically synthesized based on their published sequences. An example of such a fragment is the truncated cauliflower mosaic virus 35S promoter, which retains its CAAT and TATA boxes. Other representative promoters include the nopaline synthase and ribulose 1,5 bisphosphate carboxylase promoters. The promoter fragment is further linked to the heterologous coding sequence. The 3' end of the coding sequence is fused to a polyadenylation site exemplified by, but not limited to, the nopaline synthase polyadenylation site. Furthermore, intermediate plant transformation vectors are available that contain one or more of these polyadenylation sites bordered by sequences required for plant transformation. The elements of the helianthinin URE and the heterologous coding sequences of the present invention can be subcloned into the polylinker site of a plant transformation vector to provide the chimeric genes.

The 5' flanking elements of the present invention can be derived from restriction endonuclease or exonuclease digestion of a helianthinin genomic clone. The restriction fragments that contain the helianthinin CAAT and TATA boxes are ligated in a forward orientation to a promoterless heterologous gene such as the coding sequence of β-glucuronidase (GUS). The skilled artisan will recognize that the 5' helianthinin regulatory sequences can be provided by other means, for example chemical or enzymatic synthesis. The heterologous product can be the coding sequence of any gene that can be expressed in such a construction. Such embodiments are contemplated by the present invention. The 3' end of the coding sequence is optionally fused to a polyadenylation site, exemplified by, but not limited to, the nopaline synthase polyadenylation site, or the octopine T-DNA gene 7 polyadenylation site. Alternatively, the polyadenylation site can be provided by the heterologous gene.

The 5' helianithinin regulatory elements that do not contain the TATA box can be linked in forward or reverse orientation to at least part of a plant promoter sequence, i.e. a plant promoter sequence containing at least the CAAT and TATA sequences. In a preferred embodiment, this promoter is a truncated cauliflower mosaic virus (CaMV) 35S promoter. The resulting chimeric complex can be ligated to a heterologous coding sequence and a polyadenylation sequence.

To provide regulated expression of the heterologous genes, plants are transformed with the chimeric gene constructions of this invention. Gene transfer is well known in the art as a method to express heterologous genes in transgenic plants. The tobacco plant is most commonly used as a host because it is easily regenerated, yields a large number of developing seeds per plant, and can be transformed at a high frequency with Agrobacterium-derived Ti plasmid vectors (Klee, et al. (1987) *Annu. Rev. Plant Physiol.* 38, 467). Dicotyledenous plants including cotton, oil seed rape and soybean are preferred as transgenic hosts. However, one of ordinary skill in the art will recognize that any plant that can be effectively transformed and regenerated can be used as a transgenic host in the present invention.

A variety of transformation methods are known. The chimeric genes can be introduced into plants by a leaf disk transformation-regeneration procedure as described by Horsch et al. (1985) *Science* 227, 1229). Other methods of transformation, such as protoplast culture (Horsch et al., (1984) Science 223, 496; DeBlock et al. (1984) EMBO J. 2, 2143; Barton et al. (1983) *Cell* 32, 1033) or transformation of stem or root explants in vitro (Zambryski et al. (1983) *EMBO J.* 2, 2143; Barton et al. (1983) *Cell* 32, 1033) can also be used and are within the scope of this invention. In a preferred embodiment plants are transformed with Agrobacterium-derived vectors. However, other methods are available to insert the chimeric genes of the present invention into plant cells. Such alternative methods include biolistic approaches (Klein et al. (1987) *Nature* 327, 70) electroporation, chemically-induced DNA uptake, and use of viruses or pollen as vectors.

When necessary for the transformation method, the chimeric genes of the present invention can be inserted into a plant transformation vector, e.g. the binary vector described by Bevan (1984). Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the two- inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transformation of sequences bordered by the T-region into the nuclear genomes of plants.

Surface-sterilized leaf disks are inoculated with the "disarmed" foreign DNA-containing *A. tumefaciens*, cultured for two days, and then transferred to antibiotic-containing medium. Transformed shoots are selected after rooting in medium containing the appropriate antibiotic, and transferred to soil. Transgenic plants are self-pollinated and seeds from these plants are collected and grown on antibiotic-containing medium.

Expression of a heterologous or reporter gene in developing seeds, young seedlings and mature plants can be monitored by immunological, histochemical or activity assays.

As discussed herein, the choice of an assay for expression of the chimeric gene depends upon the nature of the heterologous coding region. For example, Northern analysis can be used to assess transcription if appropriate nucleotide probes are available. If antibodies to the polypeptide encoded by the heterologous gene are available, Western analysis and immunohistochemical localization can be used to assess the production and localization of the polypeptide. Depending upon the heterologous gene, appropriate biochemical assays can be used. For example, acetyltransferases are detected by measuring acetylation of a standard substrate. The expression of an herbicide-resistance gene can be detected by determining the herbicide resistance of the transgenic plant.

Another aspect of the present invention provides transgenic plants or progeny of these plants containing the chimeric genes of the invention. Both monocotyledenous and dicotyledenous plants are contemplated. Plant cells are transformed with the chimeric genes by any of the plant transformation methods described above. The transformed plant cell, usually in a callus culture or leaf disk, is regenerated into a complete transgenic plant by methods well-known to one of ordinary skill in the art (e.g. Horsch et al. (1985) *Science* 227, 1129). In a preferred embodiment, the transgenic plant is cotton, oil seed rape, maize, tobacco, or soybean. Since progeny of transformed plants inherit the chimeric genes, seeds or cuttings from transformed plants are used to maintain the transgenic plant line.

The instant invention also provides a method for producing a plant with improved seed lipid quality. This method comprises transforming a plant cell with a vector containing a chimeric gene comprising a seed-specific regulatory element linked to the coding sequence of a lipid metabolism enzyme such as a desaturase, and selecting for a plant with the desired characteristics. In a preferred embodiment the regulatory element is provided by nucleotides 1 to 2401 or 851 to 2401 of the URE of HaC-3A as shown in SEQ ID NO:1. The transformed plant cells are regenerated into plants with improved seed lipid quality.

Another aspect of the present invention provides a method for producing a plant with improved seed protein quality. This method comprises transforming a plant cell with a vector containing a chimeric gene comprising a seed-specific regulatory element linked to the coding sequence of a seed storage protein with a high content of lysine and/or methionine residues, and selecting for a plant with the desired characteristic. In a preferred embodiment the regulatory element is provided by nucleotides 1 to 2401 or 851 to 2401 of the URE of HaG3-A as shown in SEQ ID NO:1. The transformed plant cells are regenerated into plants with improved seed protein quality.

Another aspect of the present invention provides a method for producing a herbicide-resistant plant. Plant cells are transformed with a vector containing a chimeric gene comprising a root-specific regulatory element linked to the coding sequence of a herbicide resistance gene such as a glyphosate resistance gene and then plants with the desired herbicide resistance are selected. Selected plants are those which survive a herbicide treatment which kills untransformed plants of the same kind under the same conditions. In a preferred embodiment, the regulatory element is provided by nucleotides 1 to 1639 or 851 to 1639 of the URE of HaG3-A as shown in SEQ ID NO:1, and the heterologous sequence is provided by a gene encoding EPSP synthase, acetolactase synthase, or acetohydroxy acid synthase. The transformed plant cells are regenerated into herbicide-resistant plants. In a preferred embodiment, plants are transformed by the vector pRPA-ML-803, which contains the root-specific regulatory element comprising nucleotides 851 to 1639 of HaG3-A and the aroA herbicide-resistance gene.

The following examples further illustrate the invention.

EXAMPLE 1

General Methods

The nucleotide sequences referred to in the following examples are numbered according to FIG. 1–3.

GUS Reporter Gene Constructions

The general purpose GUS reporter cassettes used throughout the examples have been described previously (Jefferson et al. (1987) *EMBO J.* 6, 3901). Briefly, the coding region of GUS was ligated 5' of the nopaline synthase polyadenylation site in the polylinker site of the *A. tumefaciens*-derived vector pBIN19 (Bevan (1984) *Nucleic Acids Res.* 12, 8711). The vector pBIN19 contains the left and right borders of T-DNA necessary for plant transformation, and a kanamycin resistance gene. The resulting construction, pBI101.1, is depicted in FIG. 4. Unique restriction sites upstream of the AUG initiation codon of GUS allow the insertion of promoter DNA fragments.

The CaMV 35S promoter was ligated into the HindIII and BamHI sites of pBI101.1 to create pBI121.1, depicted in FIG. 4. To create pBI120, the CaMV 35S promoter was truncated at an EcoRV site at −90 (leaving the CAAT and TATA boxes) and cloned into the polylinker site of pBI101.1.

Figure 5:
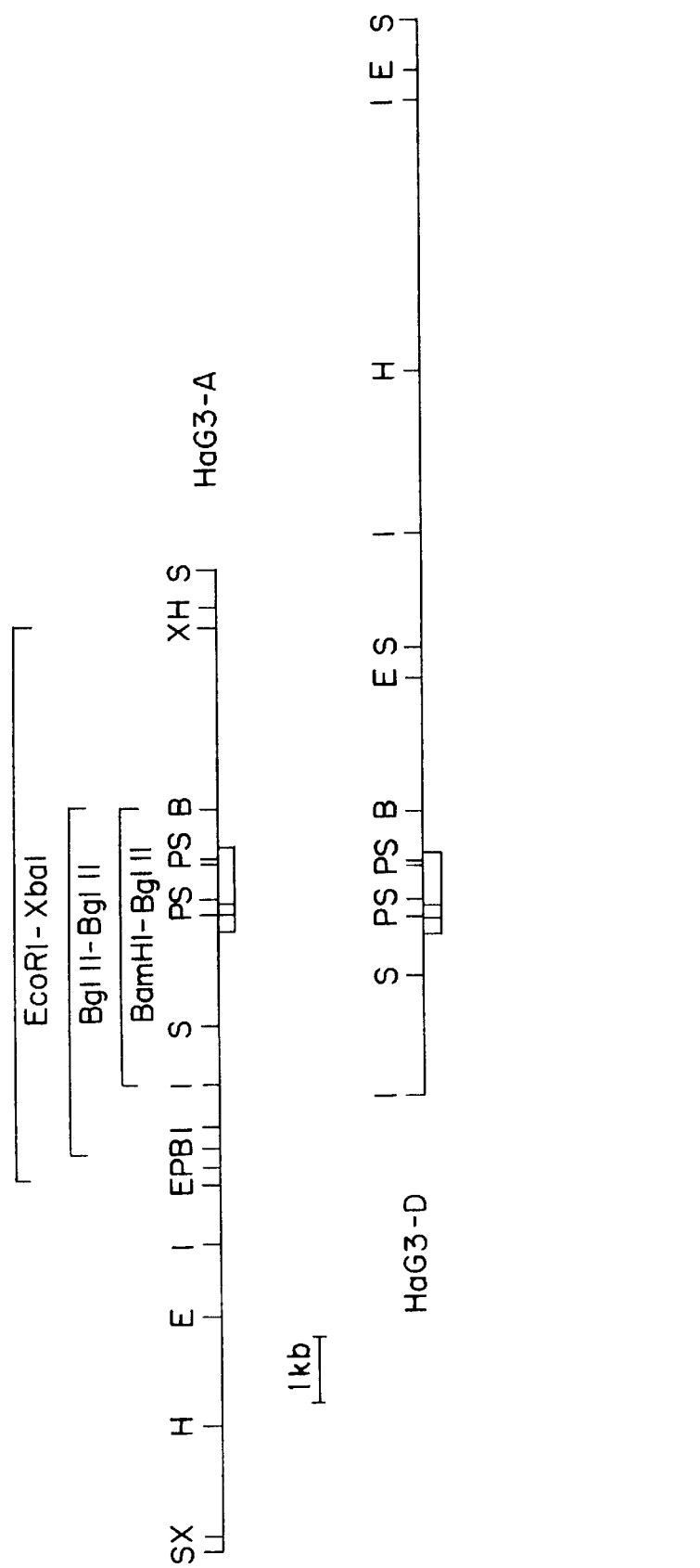
FIG. 5 depicts a restriction map of helianthinin genomic clones HaG3-A and HaG3-D and the restriction fragments used to construct the parental plasmids.
Figure 6:
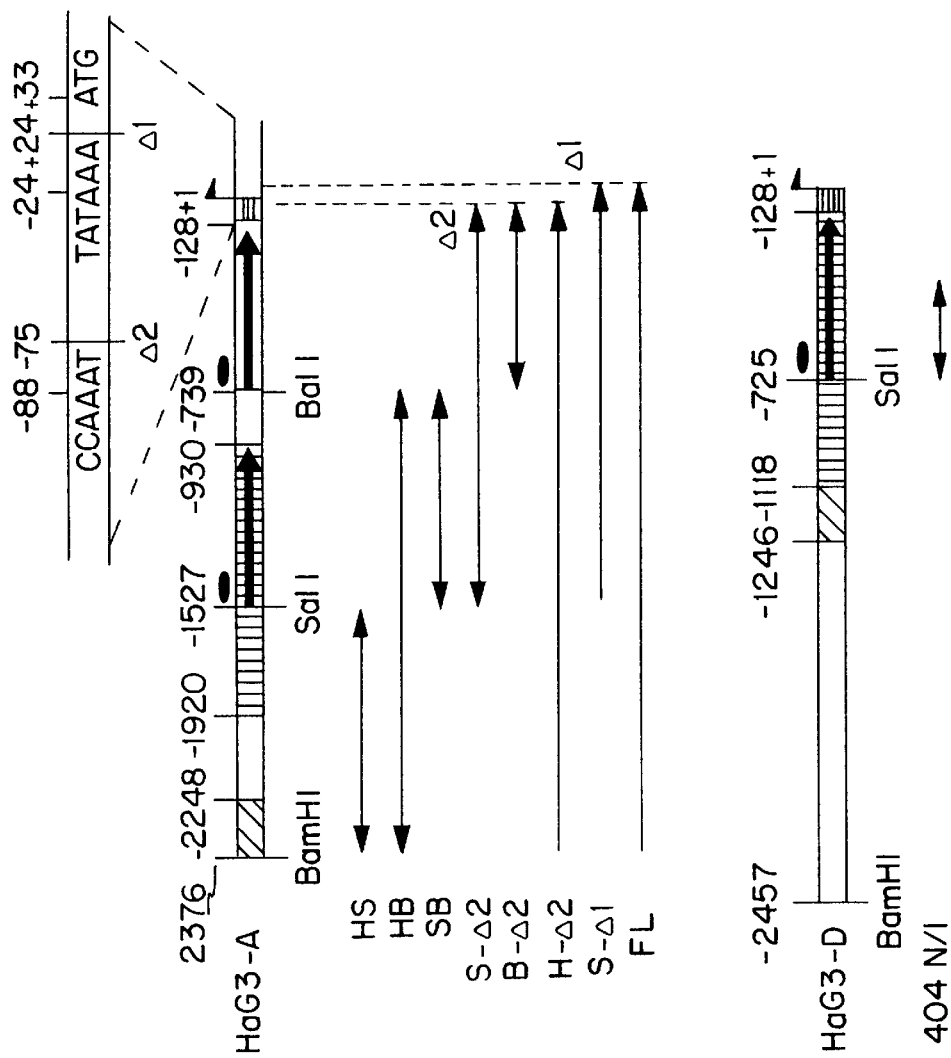
FIG. 6 depicts t-be HaG3-A and HaG3-D derivative constructions in relation to the full length construction.

Table 1 describes the parental plasmids and derivative constructions. HaG3-A-FL and the control constructions pBI121.1 and pBI101.1 are depicted in FIG. 4. FIG. 5 shows the restriction fragments of genomic clones HaG3-A and HaG3-D used to construct parental plasmids. FIG. 6 shows the derivative constructions schematically in relation to the full length construction. The HaG3-A/GUS constructions represent large overlapping fragments that span the full length regulatory region (−2377 to +24 of FIG. 1). The 3' ends of several constructions were derived from exonuclease III digestions of a 2.8 kb HaG3-A fragment in pbluescript (Stratagene) [pHaG3-A-2.3 (BamHI-PstI), Table 1]. These deletions are shown at the top of FIG. 4. The first deletion, pHaG3-A-2.4, contains the HaG3-A CAAT and TATA boxes with its 3' end at −75. Fragments that contained the HaG3-A CAAT and TATA boxes were ligated in forward orientation into the promoterless GUS cassette pBI101.1. Fragments that did not contain the HaG3-A TATA box were ligated in both orientations upstream of the truncated CAMV 35S promoter of pBI120. These fragments were subcloned into the appropriate GUS cassette. Constructions are named according to their end sites followed by an F, indicating forward orientation; R, indicating reverse orientation. Arrows indicate the orientation of the fragment with respect to the GUS coding region (FIG. 4). The HaG3-D/GUS constructions contain a 404 bp fragment (Sal1-Hpa1) in both orientations: Normal (N) and Inverse (I). The accuracy and orientation of each construction was confirmed by double-stranded dideoxy sequencing (Chen and Seeburg, 1985) using primers to regions in the GUS cassettes (Advanced DNA Technologies Lab, Texas A&M University).

Plant Transformation

The BIN-19 based plasmid constructions were used to transform tobacco (*Nicotiana tabacum* cv. Xanthi) according to standard procedures (Horsch et al. 1985) except that initial transformants were selected on 50 µg kanamycin/ml and then were transferred to 100 µg/ml kanamycin. Plants were self-pollinated, and seeds were germinated on kanamycin (400 g/ml) to identify transformants, since the BIN-19 based constructions contain the neomycin phosphotransferase gene (NPTII), which confers resistance to the toxic antibiotic kanamycin. The copy number of each GUS construction integrated into the tobacco genome was estimated for each transformant by segregation frequencies of the NPTII gene. Most of the transformants contained only one segregating locus of the construction. Filial, homozygous plants were used where indicated. Transgenic plants representing all of the test constructions were obtained except for the reverse construction of H-Δ2. Transgenic plants were maintained in Conviron chambers: 16 h light:8 h dark, 24° C., 70–80% relative humidity. All plants were watered on a strict schedule to prevent desiccation prior to testing.

TABLE 1

| Construction | Description |
|---|---|
| Parental Plasmids | |
| pBI101.1 | Bin 19-derived promoterless GUS reporter gene cassette. |
| pBI121.1 | CaMV 35S promoter fused to GUS cassette in pBI 101.1. |
| pBI120 | CaMV 35S promoter truncated at EcoRV site, leaving CAAT and TATA boxes, fused to GUS coding region. |
| pHaG3-A-2.8 | 2.8 kb BamIH-PstI fragment of Hag3-A in pBluescript; contains 2.4 kb upstream of HaG3-A coding region and 0.38 kb downstream of transcription start site; used to generate exonuclease III deletions. |
| pHaG3-A-2.4 | 2.4 kb HaG3-A fragment generated from 3' exonuclease III digestion of pHaG3A-2.8 to +24; contains the HaG3-A CAAT and TATA boxes. |

TABLE 1-continued

| Construction | Description |
|---|---|
| pHaG3-A-2.3 | 2.3 kb HaG3-A fragment generated from 3' exonuclease III digestion of pHaG3A-2.8 to −75; contains the HaG3-A CAAT box. |
| | Derivative Constructions |
| HaG3-A-FL | 2.4 kb insert of pHaG3A-2.4 fused to pBI101.1 in forward orientation |
| HaG3-A-HS/F -HS/R | 0.85 kb BamH1-SalI fragment from pHaG3A-2.3 cloned in forward and reverse orientation with respect to the truncated CaMV 35S promoter of pBI120. |
| HAG3-A-HS/R | 0.85 kb excised as a SacI fragment from HaG3A-HS/F and cloned in reverse orientation with respect to the truncated CaMV 35S promoter pBI 120. |
| HaG3-A-HB/F -HB/R | 1.6 kb BamH1-BalI fragment from pHaG3A-2.3 cloned in forward and reverse orientations with respect to the truncated CaMV 35S promoter pBI 120. |
| HaG3-A-S 2/F -S 2/R | 0.6 kb SalI-BalI from HaG3-A cloned in forward and reverse orientations with respect to the truncated CaMV 35S promoter of pBI120; constructed by deleting SalI-BamH1 fragment from HaG3-A-HB/F and HaG3-A-HB/R, respectively. |
| HaG3-A-S 2/F -S 2/R | 1.4 kb SalI fragment from pHaG3-A-2.3 cloned in forward and reverse orientation with respect to the truncated CaMV 35S promoter in pBI120. |
| HaG3-A-B 2/F -B 2/R | 0.66 kb BalI SalI fragment from pHaG3-A-2.3 cloned in forward and reverse orientation with respect to the truncated CaMV 35S promoter in pBI120. |
| HaG3-A-HΔ2 | 2.3 kb insert from pHaG3-A-2.3 cloned in forward orientation with respect to the truncated CaMV 35S promoter of pBI120. |
| HaG3-A-SΔ1 | 1.5 kb SalI fragment from pHaG3-A-2.4 cloned in forward orientation with respect to pBI 101.1. |
| HaG3-D-404N -404I | 0.4 kb SalI-HpaI fragment form HaG3-D cloned in forward and reverse orientation with respect to the truncated CaMV 35S promoter in pBI120. |

EXAMPLE 2

Biochemical Detection of GUS Activity: Seed-Specific and Root-Specific Expression GUS activity was determined in embryonic and non-embryonic tissues of transgenic tobacco containing each construction of Table 1. The standard procedures of Jefferson et al. (1987) were followed.

Plant tissue was ground in extraction buffer (50 mM $NaPO_4$, 10 mM EDTA, 0.1% Sarkosyl, 0.1% Triton X-100 and 10 mM β-mercaptoethanol). After centrifugation of the lysate, the supernatant was removed to a fresh tube and dispensed in 100 μl aliquots. An equal volume of 2 mM 4-mathlumbelliferyl-β-D-glucuronide in extraction buffer was added and allowed to incubate at 37° C. for 1 h. Reactions were stopped with 0.8 ml $Na_2Co_3$ (0.2M). The fluorescence of the resulting 4-methylumbelliferone (4-MU) was determined with a Hoeffer TKO-100 minifluorometer as described (Jefferson et al. 1987). GUS activity is expressed in picomoles 4-MU per unit mass total protein sample per minute.

Cotyledons, hypocotyls, leaves, and roots from transgenic seedlings, ranging from 18 to 20 days post-inhibition (DPI), containing various sequence elements of HaG3-A (summarized in FIG. 4) driving GUS expression were assayed for activity. Results are provided in Table 2. All constructions containing some portion of the URE of the helianthinin genes HaG3-A and HaG3-D conferred GUS activity in transgenic tobacco seeds. The full length regulatory region (FL) and fragments derived from this region, as well as the HaG3-D/GUS constructions, all conferred significant GUS activity in mature seeds when compared with the GUS expression driven by the intact CaMV 35S promoter complex (pBI121). However, well-defined seed-specific expression was only obtained with constructs including the proximal upstream regions between −75 and +24 (cf. FL and S-Δs). These two constructions containing nucleotides −2377 to +24 or −1527 to +24 demonstrated tissue-specific GUS expression with no detectable GUS activity in any tissues of transgenic seedlings. The FL construct, however, was expressed in mature seeds at sixfold higher levels compared to S-Δ1. GUS activity in tissues of seedlings containing the intact CaMV 35S promoter complex (pBI121) are included for comparison as well as the negative controls containing the truncated CAMV 35S promoter (pBI120) or no promoter (pBI101). Compared to expression in seeds there was little expression in leaves containing the same construction; on the other hand, most constructions, other than FL and S-Δ1, demonstrated significant expression in roots of transgenic seedlings.

The overall activity conferred by the intact CaMV 35S promoter complex was higher than that conferred by all other constructions in somatic tissue except in roots. In particular, roots of seedlings containing the HB/R (−2377 to −739) and SB/R (−1527 to −739) constructions showed levels of GUS activity 7 to 8 times above that of roots expressing GUS under control of the intact CaMV 35S promoter.

TABLE 2

Summary of GUS Expression in Embryonic and Non-Embryonic Tissues of Transgenic Tobacco[a]

| CON-STRUC-TION[b] | DE-VEL-OP-MEN-TAL PRO-FILE[c] | GUS ACTIVITY SEEDS[f] | (pmole 4MU/μg/min)[e] LEAF[g] | ROOT[g] | ABA Re-sponse[h] |
|---|---|---|---|---|---|
| HaG3-A | | | | | |
| FL | I | 18.7 ± 8.7 | 0 | 0 | + |
| S-Δ1 | I | 3.4 ± 1.1 | 0 | 0 | ND |
| F HS | III | 17.1 ± 15 | 0.45 ± 0.05 | 36.6 ± 2.2 | − |
| R | ND[d] | 6.2 ± 1.0 | 0.23 ± 0.05 | 8.9 ± 1.8 | − |
| F HB | II | 14.8 ± 5.2 | 0.95 ± 0.13 | 29.9 ± 2.2 | + |
| R | ND | 13.1 ± 6.9 | 0.25 ± 0.05 | 75.4 ± 3 | − |
| F SB | II | 11.1 ± 5.8 | 0 | 13.9 ± 6.8 | − |
| R | ND | 12.1 ± 5.8 | 0.34 ± 0.05 | 90.5 ± 9.9 | + |
| F S-Δ2 | II | 35.7 ± 4.2 | 0 | 20.6 ± 10.2 | ND |
| R | ND | 21.0 ± 15 | 0.45 ± 0.08 | 38.8 ± 1.2 | + |
| F B-Δ2 | III | 11.2 ± 3.9 | 2.03 ± 0.08 | 8.0 ± 0.62 | + |
| R | ND | 7.2 ± 2.3 | 4.05 ± 0.10 | 3.9 ± 0.3 | + |
| H-Δ2 F | III | 1.8 ± 1.0 | ND | 1.8 ± 0.3 | ND |
| HaG3-D | | | | | |
| N 404 | III | 9.2 ± 2.9 | 0.07 ± 0.01 | 6.8 ± 0.5 | + |
| I | ND | 9.2 ± 3.9 | 2.03 ± 0.05 | 12.9 ± 2.8 | + |

TABLE 2-continued

Summary of GUS Expression in Embryonic and
Non-Embryonic Tissues of Transgenic Tobacco[a]

| CON-STRUC-TION[b] | DEVELOPMENTAL PROFILE[c] | GUS ACTIVITY SEEDS[f] | (pmole 4MU/μg/min)[e] LEAF[g] | ROOT[g] | ABA Response[h] |
|---|---|---|---|---|---|
| Controls | | | | | |
| pBI 101 | ND | 0 | 0 | 0 | – |
| pBI 120 | ND | 0 | 0 | 0 | – |
| pBI 121 | ND | 4.3 ± 1.0 | 22.0 ± 7.9 | 9.9 ± 4.0 | – |

[a]Mature seeds and seedling tissues of transgenic tobacco containing constructions in FIG. 6 were assayed for GUS activity.
[b]Constructions are as shown in FIG. 6. Forward (F) and Reverse (R), Normal (N) and Inverted (I), refer to the orientation of each helianthinin fragment with respect to the truncated 35S CaMv promoter.
[c]Developing seeds of transgenic tobacco containing forward constructions in FIG. 6 were assayed for GUS activity at approximately 2 days intervals from 8–24 DPF. Type I, II and III profiles are defined in Example 3.
[d]ND, not determined in this experimental series.
[e]In all experiments, GUS assays represent averages from four to ten independently transformed plants for each construction. Standard deviations are included.
[f]GUS activity in mature (30 DPF) transgenic tobacco seeds.
[g]Transgenic tobacco seedlings were grown axenically on solid medium. Tissues from seedlings (18–20 DPI) were collected and assayed for GUS activity.
[h]FL ABA responsive only in developing seeds 12–18 DPF (see text and Table 3). All others, ABA response predicted from GUS expression of dessicated leaves and subsequent demonstration that seedlings of indicated plants respond directly to exogenous ABA. Plus sign indicates induction of GUS activity over basal level. Minus sign indicates no detectable induction of GUS activity.

EXAMPLE 3

Biochemical Detection of GUS Activity
Temporally-Regulated Expression

The temporal profile conferred by each forward construction was determined and the results are shown in Table 2. Filial homozygous plants were grown and allowed to flower, and seeds from staged pods were assayed for GUS expression as described in Example 2. Three types of developmental profiles were identified based on the time of initial appearance of GUS activity in developing embryos and the qualitative and quantitative characteristics of the resulting expression patterns; Type I profiles showed correct temporal regulation where accumulation of GUS begins 12 DPF. In plants exhibiting Type II profiles, GUS activity also began accumulating around 12 DPF but peaked around 14 DPF followed by significant declines in levels of GUS activity. Type III plants showed activity occurring before 10 DPF with a peak of activity occurring at approximately 12 DPF. Constructions containing the regions of the HaG3-A URE from nucleotides −2377 to −1527 or −739 to −75 conferred this temporally earlier profile.

EXAMPLE 4

Histochemical Localization of GUS Activity

GUS activity was histochemically localized in seedlings containing HaG3-A-SB/R and HaG3-D-404N. Samples were washed in 50 mM NaPO$_4$ and incubated for 24 h at 37° C. in 100 μl reaction buffer [50 mM NaPO$_4$, pH 7.0, 2 mM 5-bromo-4-chloro-3-indolyl-glucuronide (X-Gluc), 0.1 mM potassium ferricyanide, and 0.1 mM potassium ferricyanide, and 0.1 mM potassium ferrocyanide]. Samples were mounted on microscope slides with 80% glycerol.

Figure 7A:
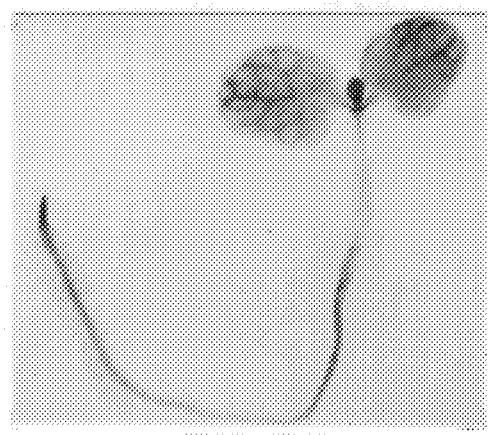
FIG. 7 demonstrates histochemical localization of GUS activity in transgenic seedlings containing the HaG3-D-N and HaG3-A-SB/R constructions. A: HaG3-D-404N, 8 days post-imbibition (DPI); B: HaG3-A-SB/R, 8 DPI; C: HaG3-D-404N, 14 DPI; D: HaG3-A-SB/R, 14 DPI; E: HaG3-A-SB/R, 8 DPI; F: HaG3-A-SB/R, 6 DPI.
Figure 7B:
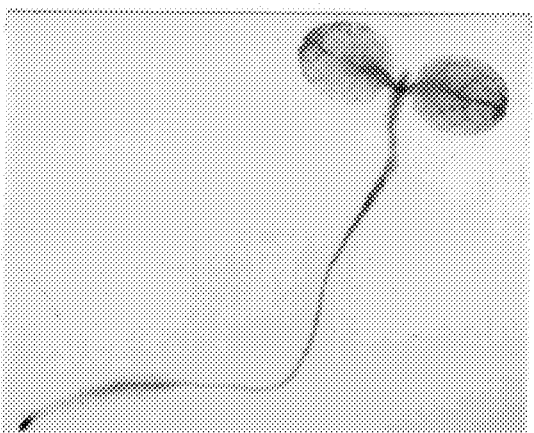
Figure 7C:
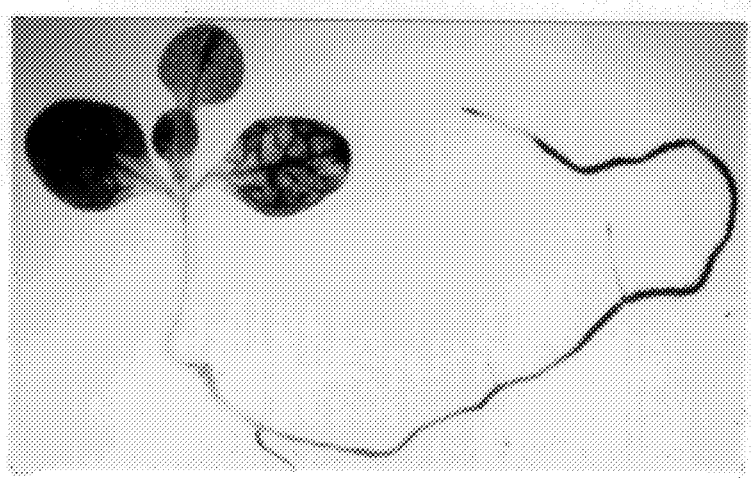

HaG3-D-404N (FIG. 7A) and HaG3-A-SB/R (FIG. 7B) seedlings grown on basal media containing 1% sucrose showed slightly different patterns of expression. HaG3-D-N driven GUS expression appeared at low levels in the cotyledons and at significantly higher levels in the distal root region with no detectable activity in the hypocotyl. The HaG3-A-SB/R seedling also showed significant GUS activity in the distal root with no detectable activity in the hypocotyl or cotyledons. GUS activity was histochemically localized at 14 DPI in seedlings containing HaG3-D-404N that were grown in a water-deficient environment on sub-saturated filter paper; GUS activity was primarily in the leaves and roots of these seedlings (FIG. 7C).

Figure 7D:
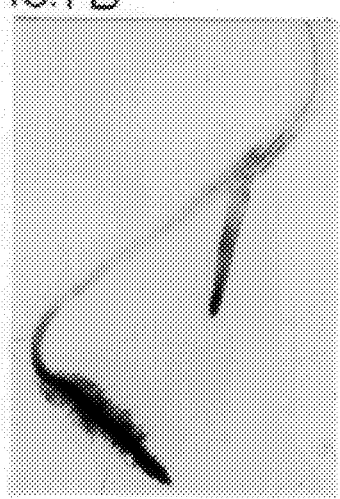
Figure 7E:
Figure 7F:

The GUS expression patterns of seedlings containing HaG3-A-SB/R was determined. The major site of GUS activity in the SB/R seedling was in the developing root tips (FIG. 7B, C). In 6 DPI seedlings containing HaG3-A-SB/R, GUS was expressed throughout the length of the elongating root with particularly high levels in the meristematic region of the root tip (FIG. 7D). Histochemical localization of HaG3-A-SB/R seedlings (14 DPI) showed activity in newly formed lateral roots as well as the continued activity in the meristematic region of the main root (FIG. 7B). Seedlings from 16 DPI continued to show this pattern of expression (FIG. 7C); root hairs and the distal portions of the root had high levels of GUS activity as well.

EXAMPLE 5

ABA-Responsive Expression

In a series of whole plant experiments on transgenic tobacco containing constructions illustrated in FIG. 4, several regions of the UREs of HaG3-A and HaG3-D were identified that responded to changes in the plants water potential (Table 2). Since ABA is a known mediator of water-deficit responses, the effect of ABA on GUS expression driven by these elements was determined. Within HaG3-A, two regions (−1527 to −739 and −739 to −75) were shown to confer ABA-responsive expression in leaves of mature transgenic tobacco and in seedlings. Another ABA-responsive element was identified in the URE of HaG3-D (−739 to −322).

Figure 8A:
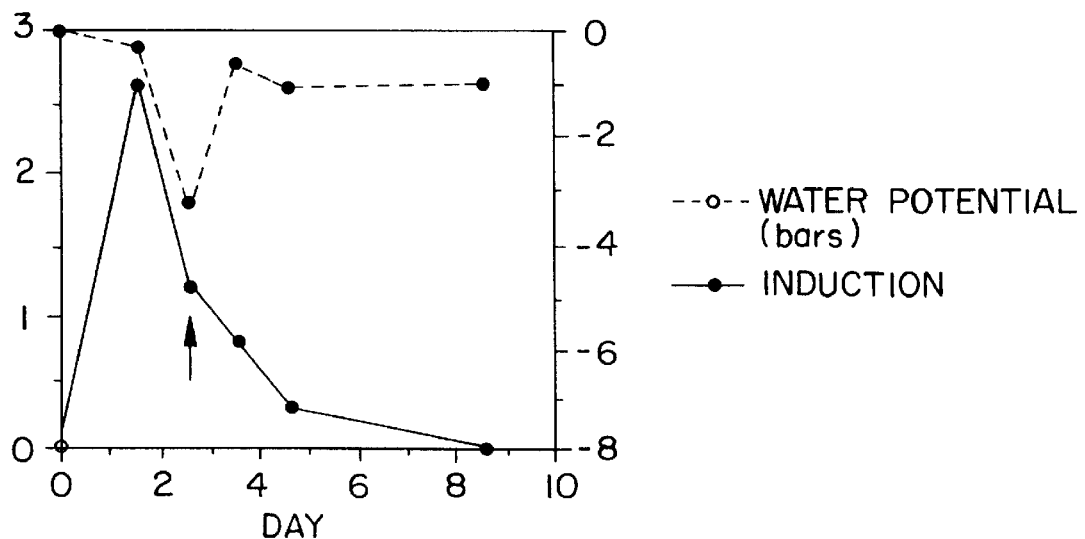
FIG. 8 graphically illustrates the induction of GUS activity in transgenic tobacco leaves containing HaG3-D-404N during progressive desiccation and subsequent recovery from water deficit.
Figure 8B:
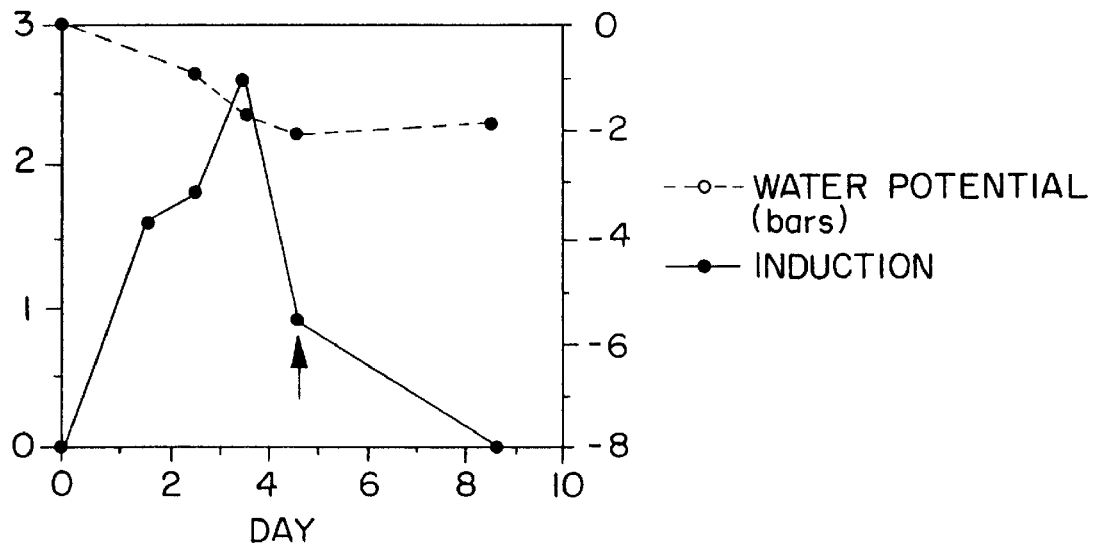

The induction of GUS activity in transgenic tobacco containing HaG3-D-404N (forward orientation) was correlated with water potential during processive desiccation and subsequent recovery from water deficit. Since the full length HaG3-A LAE is not expressed under any conditions except during seed development, plants containing this chimeric CJS construction were used as negative controls. Filial, homozygous plants containing each construction were grown in soil. Plants were either watered normally (control) or stressed to varying degrees by watering with ⅓ the amount of the control plant or by not watering at all. Fully stressed plants containing HaG3-D-404N were induced rapidly with a peak of GUS activity at about 36 hours, which correlated with a decrease in water potential (FIG. 8). Subsequent GUS determinations 24 hours later revealed a reproducible decrease in GUS activity even though the plants were under severe water-deficit with water potential of nearly −4 bars. The fully stressed plants were recovered by watering after sampling was completed on day 3. The plants recovered quickly as the water potential returned to non-stressed levels after watering, and GUS activity continued to decrease over the remaining dams. GUS activity in ⅓ stressed plants containing HaG2-D-N increased more moderately during a 3.5 day interval as the water potential decreased (FIG. 8). As observed with fully stressed plants, GUS activity decreased before water-deficit recovery. In no instance did the FL plants express GUS in non-embryonic tissues.

Figure 9:
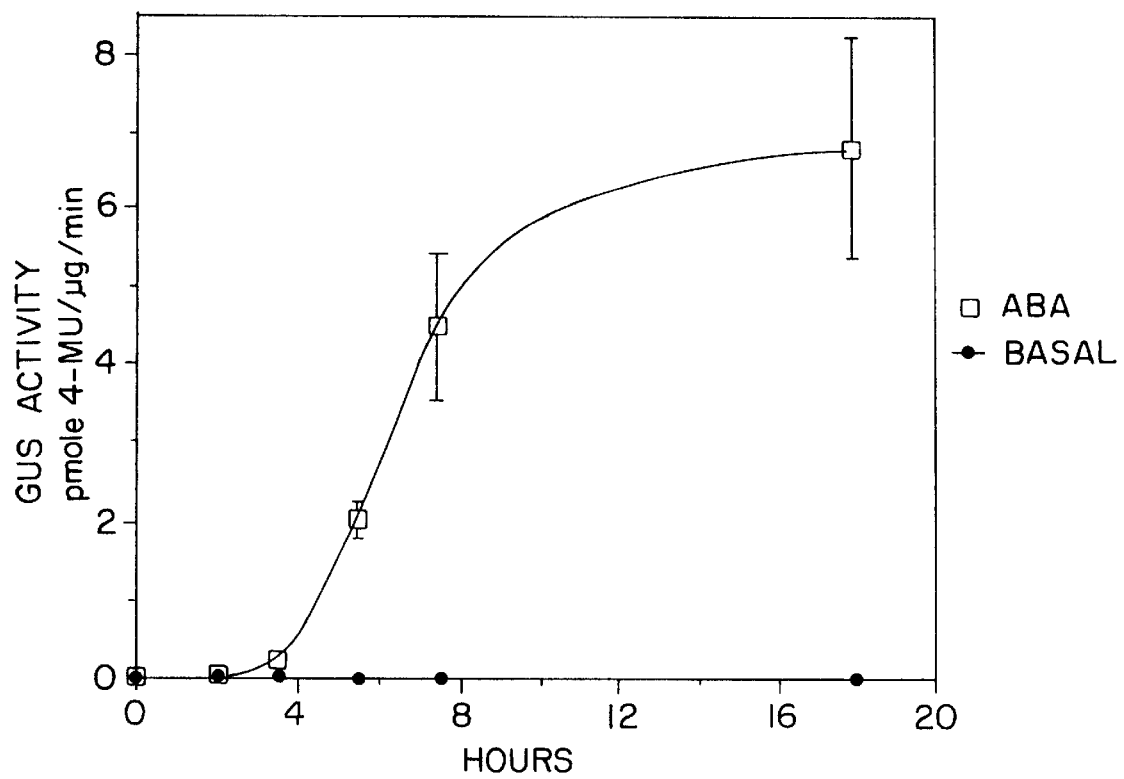
FIG. 9 is a graph depicting ABA induction of GUS expression in leaves of tobacco containing HaG3-D-404N.

To determine if the 404 bp fragment from HaG3-D responds directly to ABA, leaf disks of transgenic tobacco containing HaG3-D-404N were treated with ABA for increasing periods of time and were subsequently assayed for GUS expression. After a lag-time of approximately 3.5 hours, treatment with 10 mM ABA resulted in a rapid increase in GUS expression; GUS continued to accumulate through eight hours at which time the rate of accumulation decreased significantly (FIG. 9). There was no detectable GUS activity in leaf disks from the same plant maintained under identical conditions exclusive of ABA. Likewise, leaf disks from plants containing the HaG3-A full length URE showed no activity during the course of the experiment. Since the chimeric gene including the CaMV35S promoter and the β-glucuronidase reporter gene is transcriptionally active in leaves (Table 1), transgenic plants containing pBI121 served as an important negative control. Leaf disks from plants containing pBI121 showed no increase in GUS activity in response to exogenous ABA throughout the experiment (+ABA: 12.6±3.3 pmole 4-MU/μg/min; -ABA: 13.5±3.6 pmole 4-MU/lg/min).

A similar series of experiments was carried out with transgenic tobacco seedlings containing HaG3-D-404N and HaG3-A-FL (FIG. 4). Eighteen DPI seedlings were transferred to media containing 0–10 mM ABA, and GUS activity was determined one, two and three days later (Table 3). Seedlings containing HaG3-D-404N were inducible by ABA by day 1 at all ABA concentrations; there was no significant induction of HaG3-A-FL in parallel experiments. Induction was concentration and time dependent. Maximum induction, exceeding 200 fold, occurred at two and three days at ABA concentrations of 10 mM (Table 3). Significant induction of 19 and 70 fold occurred on day three at 0.1 mM and 1.0 mM ABA, respectively.

The full-length (FL) helianthinin HaG3-A URE (-2377 to +24) was tested for its inducibility by ABA in developing seeds. Seeds containing the full length (FL) regulatory region driving the expression of GUS (FIG. 4) were staged at 11, 14, 18 and 24 days post flowering and were tested for their ability to respond to ABA. Induction by ABA was shown by the increased levels of GUS activity over levels obtained on basal media; results are summarized in Table 3. ABA responsiveness varied with the stage of development. Seeds from 11 DPF did not respond to ABA during the course of the experiment whereas more mature seeds did respond. Seeds from 14 DPF responded rapidly with induction above basal levels beginning as early as 1.5 hours. There was a monotonic increase in GUS activity with 14 DPF seeds treated with ABA; by three days of treatment, the levels of GUS activity were higher than that for 18 and 24 DPF seeds treated with or without ABA. Seeds from 18 DPF were slower to respond to ABA than those from 14 DPF, but levels of GUS activity comparable to 14 DPF (+ABA) seeds were observed in 18 DPF seeds by the fifth day of ABA treatment. Seeds from 24 DPF are less responsive to ABA through five days of ABA treatment. Levels of GUS activity also varied with seeds incubated on basal media alone. Seeds from 14 DPF on basal media continued to increase in GUS activity an estimated 4 pmol 4-MU/seed/day.

The preceeding results demonstrate a hierarchy controlling helianthinin gene expression so that the ABA-responsive elements contained within the HaG3 UREs are functional only within the context of the appropriate developmental program, i.e. seed maturation. Taking the ABA-responsive elements out of the context of the HaG3-A or HaG3-D UREs results in the loss of hierarchical control so that these elements are free to respond directly to ABA and indirectly to desiccation in leaves and seedlings of transgenic tobacco.

TABLE 3

ABA Induction In Vitro of HaG3-A-FL in in Transgenic Tobacco Seeds[a]

GUS Activity (pmole 4-MU/μg/min)
ABA

| DPF | Normal | 11 DPF + | 11 DPF − | 14 DPF + | 14 DPF − | 18 DPF + | 18 DPF − | 24 DPF + | 24 DPF − |
|-----|--------|---|---|------|------|------|------|------|------|
| 11 | 0 | 0 | 0 | — | | — | | — | |
| 14 | 7 ± 0.3 | 0 | 0 | 7.0 | 7.0 | — | | — | |
| 16 | — | 0 | 0 | — | | — | | — | |
| 17 | — | | | 33 | 15 | — | | — | |
| 18 | 15 ± 0.3 | | | — | | 15 | 15 | — | |
| 19 | — | | | 57 | 24 | — | | — | |
| 21 | — | | | — | | 24 | 15 | — | |
| 23 | — | | | — | | 61 | 15 | — | |
| 24 | 16 ± 2.0 | | | — | | — | | 16 | 15 |
| 27 | — | | | — | | — | | 21 | 16 |
| 29 | — | | | — | | — | | 24 | 16 |
| 35 | 14 ± 2.0 | | | — | | — | | — | |

[a]Transgenic tobacco seeds containing HaG3-A-FL were collected at indicated days post flowering (DPF) and were incubated on basal media alone or basal media containing 1 μM ABA. GUS activity was determined after 0, 3 and 5 days of treatment. In vivo expression of HaG3-A-FL-driven GUS in developing seeds (Normal) is shown for reference.

EXAMPLE 6

Introduction of Herbicide Tolerance into Tobacco

The 0.66 kb BalI-SalI fragment from the parental plasmid pHaG3-A-2.3 (Table 1) was linked at its 5' end to a HindIII site and at its 3' end to an EcoRI site. The resulting cassette was substituted for the double CaMV promoter region in the pRPA-BL-410 construct (described in French Patent Appln. No. 91 02872, filed March 5, 1991) by digesting pRPA-BL-410 with HindIII and EcoRI and subcloning the cassette into that vector. The resulting construct, termed pRPA-ML-803, comprises in the transcriptional frame the following elements: the helianthinin regulatory element, optimized transit peptide (OTP), aroA gene, nos terminator.

The plasmid pRPA-ML-803 was transferred into *Agrobacterium tumefaciens* strain EHA101 (Hood et al. (1986) *J. Bacteriol,* 168, 1291) by triparental mating and the resulting Agrobacterium was used for leaf disk transformation of tobacco.

Regenerated tobacco plants, about twenty centimeters tall, were sprayed in the greenhouse with glyphosate formulated as ROUNDUP at a dose of 0.6Kg of active ingredient/hectare. Untransformed control plants were killed when sprayed with this dose of glyphosate. Transformed plants, which were healthy and viable, showed enhanced tolerance to glyphosate exposure.

What is claimed:

1. A chimeric plant gene comprising at least one regulatory element from a helianthinin gene that directs ABA-responsive gene expression wherein said element is operably linked to the coding sequence of a heterologous gene to effect said expression of a gene product from said coding sequence wherein said regulatory element is from HaG3A.

2. The chimeric plant gene of claim 1 wherein said regulatory element directs ABA-responsive gene expression and comprises nucleotides 1 to 2401 of SEQ ID NO:1, nucleotides 851 to 1639 of SEQ ID NO:1, or nucleotides 1639 to 2303 of SEQ ID NO:1.

3. The chimeric plant gene of claim 1 comprising a sufficient part of a promoter capable of functioning in plants and operably linked to said coding sequence and said regulatory element to effect expression of said heterologous gene.

4. The chimeric plant gene of claim 3 wherein said promoter is a plant virus promoter.

5. The chimeric plant gene of claim 4 wherein said promoter is the cauliflower mosaic virus (CAMV) 35S promoter.

6. The chimeric plant gene of claim 5 wherein said promoter is the CaMV 35S promoter comprising CAAT and TATA sequences.

7. The chimeric plant gene of claim 1 wherein said heterologous gene is a herbicide resistance gene.

8. The chimeric plant gene of claim 7 wherein said herbicide resistance gene is a glyphosate resistance gene or a gene encoding 5' enolpyruvylshikimic acid-3-phosphate synthase, acetolactase synthase, or acetohydroxy acid synthase.

9. The chimeric gene of claim 8 wherein said glyphosate resistance gene is aroA.

10. The chimeric gene of claim 9 which comprises the chimeric plant gene of pRPA-ML-803.

11. A plant transformation vector which comprises the chimeric plant gene of claim 1.

12. A plant cell comprising the transformation vector of claim 11.

13. A plant, or a progeny of said plant, which has been regenerated from the plant cell of claim 12.

14. A transgenic plant, or a progeny of said plant, comprising the chimeric plant gene of claim 1.

15. The plant of claim 13 wherein said plant is a cotton, tobacco, oil seed rape, maize or soybean plant.

16. The plant of claim 14 wherein said plant is a cotton, tobacco, oil seed rape, maize or soybean plant.

17. The plant cell of claim 12 wherein said plant cell is a cotton, tobacco, oil seed rape, maize or soybean plant cell.

18. The plant of claim 14 wherein said plant exhibits resistance to a herbicide.

19. The plant of claim 18 wherein said herbicide is glyphosate.

20. The plant of claim 19 which comprises the vector pRPA-ML-803.

21. The plant cell of claim 12 wherein said vector is pRPA-ML-803.

22. A glyphosate-resistant transgenic plant, or a progeny of said plant, which comprises the vector pRPA-ML-803.

23. The plant of claim 22 wherein said plant is a cotton, tobacco, oil seed rape, maize or soybean plant.

24. A Method for producing a plant which exhibits resistance to a herbicide which comprises:

a) transforming a plant cell with the transformation vector of claim 11; and b) regenerating said plant from said transformed plant cell.

25. The method according to claim 24 wherein the herbicide is glyphosate.

26. The method according to claim 25 wherein the vector is pRPA-ML-803.

27. An isolated nucleic acid from a helianthinin gene comprising at least one isolated regulatory element whch directs abscisic acid (ABA)-responsive gene expression wherein said gene is HaG3A.

28. The nucleic acid of claim 27 wherein the regulatory element whch directs ABA-responsive gene expression is characterized in that expression of a gene under its control is detectable in response to treatment with ABA or conditions which induce ABA biosynthesis.

29. The nucleic acid of claim 27 or 28 wherein said regulatory element directs ABA-responsive gene expression and comprises nucleotides 1 to 2401 of SEQ ID NO:1, nucleotides 851 to 1639 of SEQ NO:1, nucleotides 1639 to 2303 of SEQ ID NO:1 or nucleotides 1 to 404 of SEQ ID NO:3.

30. An isolated nucleic acid that directs ABA-responsive gene expression comprising nucleotides 1 to 2401 of SEQ ID NO:1, nucleotides 851 to 1639 to SEQ ID NO:1, or nucleotides 1639 to 2303 of SEQ ID NO:1.

31. The chimeric plant gene of claim 1 wherein said heterologous gene is a gene encoding a lipid metabolism enzyme.

32. The chimeric plant gene of claim 31 wherein said lipid metabolism enzyme is a desaturase.

33. A plant transformation vector which comprises the nucleic acid of claim 27.

34. A plant cell comprising the nucleic acid of claim 27.

35. A plant, or a progeny of said plant, which has been regenerated from the plant cell of claim 34.

36. A transgenic plant, or a progeny of said plant, comprising the nucleic acid of claim 27.

37. The plant of claims 35 or 36 wherein said plant is a cotton, tobacco, oil seed rape, maize or soybean plant.

38. The plant cell of claim 34 wherein said plant cell is a cotton, tobacco, oil seed rape, maize or soybean plant cell.

39. A plant, or a progeny of said plant, which comprises the chimeric gene of claim 31.

* * * * *

UNITED STATES PATENT AND TRADEMARK OFFICE
CERTIFICATE OF CORRECTION

PATENT NO. : 5,824,865
DATED : October 20, 1998
INVENTOR(S) : Terry Thomas, et al.

It is certified that error appears in the above-identified patent and that said Letters Patent are hereby corrected as shown below:

Column 1, Line 11: "Intention" should read --Invention--

Column 3, Line 64: "t-he" should read --the--

Column 5, Line 17: "mPNA" should read --mRNA--

Column 8, Line 49: "Saxbrook" should read --Sambrook--

Column 9, Line 28 : "helianithin" should read --helianthinin--

Column 25, Line 4, Claim 28: "whch" should read --which--

Signed and Sealed this

Twenty-ninth Day of May, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2401 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:1:

```
GGATCCTCTA  CCTATATATA  TATATATATA  TGAATTTTTT  AAAAAAATCC  CGTACCCTC     60
GAAAAAACGG  GCCTTATGCG  GAAGTCCTCC  TCGCACACCT  AAAGAGCCGC  CCATGCTTTT   120
TAATCAAATA  GATGTGCATC  ATGTAGTGAT  AGTTTTTACT  AAAATCCATT  AGTTTATAAA   180
TATTTTAAAT  GTTTTTTTTT  GTTATATAA   AAAAGAAAA   TTAAAAAACA  AAATGTCCAA   240
AATACTCCTG  TATCAACTAT  GCAAAAGAC   AAAAAAACCC  TTTTGGTTAA  CAAAGTCTTT   300
AATTTAACTA  AGTTTGTCAT  TTGAAGGAAA  TTCAAACAAA  AACGAACGTG  GGGGCGCGGG   360
GGTGGGGTGT  TTGGTTACAA  AAAGTTTTAA  TTTTAGATTA  AAGTATAAAA  ATTGCCCAAA   420
CCTCAGGACA  ATTTTTACAT  TTATAACTCA  TTGTCTAAAT  ACTAAATAC   ACCAAGTCAA   480
TGGGTGAAAG  TTACTATCTT  TTTTATTGCA  ATTTCACATT  ACCTTATTTA  CTTTTGAGAA   540
AGACGACATA  ACAATTAAGG  AGTTATAGTC  TGATCGGTTT  GCGCTATTTT  TCATACTTAA   600
GGTCCAGGTT  TGAATCTTTT  AAACATTTTT  TTTAACTTG   ATCATAACAA  TATAACAATT   660
AAGGAGTTAT  GATCTGATGG  TTTGCGTTAT  GTTTTCGTAC  TAATTAAGGT  CCCGGTTTGA   720
ATCTCTCAAA  CAATATATTA  TTTTTTCTTA  AAAACGAATG  AGACATGCTC  ACAATGGGAA   780
TTGAACCGAC  ACCTATTGGT  TTAAAATTAA  AGCTATAACA  AACTGAGCTA  CACATTTTA    840
ATTTAAAAAT  GTCGACTATC  TTAGTTAATC  AAATAAATTT  ATTTGATTT   GTTTGTTAA    900
TGTATTTTCT  CCTAATTTAA  AGTCGATGTG  TATTTATATA  ATATTAGTAA  TATTTTATTA   960
ACATCAATAC  ATGCTTCAGG  TTTTGTGTTA  GTCTTCGTTT  TTTATATGGT  TTTATCAGTG  1020
GTGTGGTGTA  CGATGACGAT  TATTTAAATA  ATGACGAACT  TCTTGGTTGT  TACTTATTGA  1080
TGTACGAAGC  TGAGATGTAA  CGAACCGAAC  ACATATAAAT  AACATTTTGG  ATAAGATTAC  1140
GACTTTATTT  ATCGGTTGCC  ATGAAATTTA  GAAGATTTGG  GTTAAGACAC  AACCACATAT  1200
AATGTGATGG  TAAATAGCAT  TTACAACTAA  TGTTAATCTT  TTGTTACAAA  TGTTGTTAAC  1260
TAGGCTTGAT  ATGTAAAATT  TTTAAAGACT  ATCAGGTGTT  CTTACGGTTT  TACATCTAGT  1320
AAGAGATTAA  AAAAAAAAAA  GCAAGGAAAG  TAAGTGTAAA  GAGAGTAAAG  AGAATGTAGC  1380
CATGATATGG  CTGATTGTTC  ATCACCATCC  CATTTATACT  TATCATCTTG  ATGATGCATA  1440
TAGACATGAT  GTGTGCTACG  TACCGAATTT  TAACAGCTTC  CCGGCGCAAC  ACACGTGTAT  1500
AAATACCATA  GATTATAAAC  CAAATACGCT  ACGTATAGGT  GGTTATATGA  TACCTATGAT  1560
GACTTGACCT  TTCGTTACAC  TTGAGCTGAA  AAAAATAAAA  AAATGTGGCT  ATAGGCGCAT  1620
GGTCACAGTT  TTTTTGTGTG  GCCATATACA  ATTTTGACG   TAGCGTTAGT  TAATCAGATA  1680
AATTTATTTT  GATTGTTTT   GTTAATGTAT  TTTCTCCTAA  TTTCAAGTAG  ACGTGTATTT  1740
ATATAATATT  AGTAATATTT  TATTAACATC  AATACATGCT  TCATGTTTTG  GGTTAGTCTT  1800
CGTTTTTTAT  ATGGTTTTAT  CAGTGGTGTA  CGATGACGAT  TATTTAAATA  ATGACGGACT  1860
```

-continued

| | | | | | | |
|---|---|---|---|---|---|---|
| TCTTGGTTGT | TACTTATTGA | TGTACGAAGC | TGAGATGTAA | CGAACCGAAC | ACATATAAAT | 1920 |
| AACATTTTGG | ATAAGATTAC | GACTTTATTT | ATCGGTTGCC | ATGAAATTTG | GAAGACTTGG | 1980 |
| GTTAAGACAC | AACCACATAT | AATGTGATGG | TAAATAGCAT | TTACAACTAA | TGTTAATCTT | 2040 |
| TTGTTACAAA | TGTTGTTAAC | TAGGCTTGAT | ATGTAAAATT | TTTAAAGACT | ATATGGTGTT | 2100 |
| CTTACGGTTT | TACATCTAGT | AAGAGATTAA | AAAAAAAAA | AAAAGCAAGG | AAAGTAAGTG | 2160 |
| TAAAGAGAGT | AAAGAGAATG | TAGCCATGAT | ATGGCTGATT | GTTCATCACC | ATCCCATTTA | 2220 |
| TACTTATCAT | CTTGATGATG | CATATAGACA | AACACACTAC | TTATACAGAT | GTAGCATGTC | 2280 |
| TCAGCTCCAA | ATGGTGATCT | TCTCCTGGCA | TAACCTCTTA | GATGTCACTT | CCTCCTTGAT | 2340 |
| CTTCTTCCAC | TATAAAACCA | GCTAGTTCAC | AACACCTATT | CACCACATCA | CATCCCATTC | 2400 |
| C | | | | | | 2401 |

(2) INFORMATION FOR SEQ ID NO:2:

(i) SEQUENCE CHARACTERISTICS:
        (A) LENGTH: 1732 base pairs
        (B) TYPE: nucleic acid
        (C) STRANDEDNESS: both
        (D) TOPOLOGY: linear (xi) SEQUENCE DESCRIPTION: SEQ ID NO:2:

| | | | | | | |
|---|---|---|---|---|---|---|
| GGATCCTGTA | AGAAGTGCCC | AAAATGTGAG | AAGTGTATTA | TAACACTATA | TATAATACTA | 60 |
| TATAACACCA | TATAAATACC | GTATAACACT | ATGTAACACC | ATATAACACA | ATATAACGCT | 120 |
| ATGTAACACT | ATATAACATT | ATATAACAAT | ATATAACACT | ATACATCTAT | CAGAGACATG | 180 |
| CTATCAGACA | ACCTATAGTG | TTATATTTGT | TATATAATGT | TATATAGTGT | TACATAGCGT | 240 |
| TATATGGTAT | TATATGGTGT | TACATATTGT | TATACGTGTT | TATATGGTGT | TATATAGTAT | 300 |
| TATATATAGT | GTTATAATAC | ACTTCTCACA | CTTTGGGCAC | TTTTTACAGG | ATCATCTACC | 360 |
| TATATATATA | TATATATATA | TAAAGGATTA | GGTTCAAACG | TGAACAAATT | CCCAAGAGTG | 420 |
| AACTGCGTGA | ACTGATCTCA | GCCCTTGATT | TTTATGATCT | TGAGATTAAA | GTGAGTGGCA | 480 |
| TGATGGTAAT | TATTTGGTTA | ATTTTTTTTC | ATTTAATTAA | ATACAAAAAG | GGTATATGTG | 540 |
| TAATTTCAAT | CTTAAATTGA | TTGCATAAAT | CTCTCACAAA | TCAAGTAATC | AATTATCTTC | 600 |
| TTAAACTGAT | TACATAAATC | TCTCACAAAT | CAAATCAAGG | ATTAGGAAAG | ATGTAACTTA | 660 |
| ATTCTAATTA | CTAAAATAAC | TATTTGTTTA | AATGCGATGT | ACACATGTGT | ATTCTGATTT | 720 |
| TGCCCTCTTT | TTAATGTGAT | GTACACATGT | GTATATCGTC | TGTTTTATG | AGATCTCAGA | 780 |
| ATTTTTTTTG | TATTGAATGT | TGATGTACAC | CTGTGAATTA | CTGTACACAT | ATGTACGATG | 840 |
| CTGATGCTGA | GTACACATGT | GTACTGTTCT | ATTTATATCC | AAGTACACAT | GTGTAACCTT | 900 |
| GAAATATGAA | AGTTACGTGG | ATCTTAAAAA | TCAAAATTTG | AATTCTGGTG | ATGAAATCTG | 960 |
| AAATAAAAAT | TAAAATTGAA | ATCTGGTGAT | TTGTTGTTTG | TTTTGATAAT | TATCTTATTA | 1020 |
| ATAAATAAAC | ATAATGTGGA | TAATGAATTT | AAATTAGGAA | AGATGTAACT | TAATTCAATT | 1080 |
| ATTAAAATAA | TGATTTAAAT | CTAATTTTTT | ATATAATTAC | AATCCTACCC | TTAACAACTA | 1140 |
| AAAAGGAAAT | CAAGGGTTCA | TATCTGTTCA | CGCAGTTCAC | TCTTGGGAGG | TTGTTCACGC | 1200 |
| TGGAACCCTA | CCCTATATAT | ATATATATAT | ATATATCAAA | TTTTTTAAA | AAATCCCGTA | 1260 |
| CCCCTCGAAA | AAACGGGCCT | TATGCGGAAG | TCCTCCTCGC | ACACCTAAAG | AGCCGCCCAT | 1320 |
| GCTTTTGATC | AAATAGTTGT | AAATACTAAA | ATACACCAAG | TCAATGGGTG | AAAGTTACTA | 1380 |
| TCTTTTTTAT | TGCAATTTCA | CATTACCTTA | TTTACTTTTG | AGAAAGACGA | CATAACAATT | 1440 |
| AAGGAGTTAT | AGTCTGATCG | TTTGCGCTAT | TTTTCATACT | TAAGGTCCAG | GTTTGAATAT | 1500 |

| | | | | | |
|---|---|---|---|---|---|
| TTTAAACATT | TTTTTTAACT | TGATCATAAC | AATATAACAA | TTAAGGAGTT | ATGGTCTGAT | 1560 |
| GGTTTGCGTT | ATGTTTTCGT | ACTAATTAAG | GTCCCGGTTT | GAATCTCTCA | AACAATATAT | 1620 |
| TATTTTTACC | TAAAAACGAA | TGAGGCATGC | TCACAATGGG | AATTGAACCG | ACACCTATTG | 1680 |
| GTTTAAAATT | AAAGCTATAA | CAAACTGAGC | TACACATTTT | TAATTTAAAA | AT | 1732 |

( 2 ) INFORMATION FOR SEQ ID NO:3:

( i ) SEQUENCE CHARACTERISTICS:
        ( A ) LENGTH: 404 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:3:

| | | | | | |
|---|---|---|---|---|---|
| GTCGACTATC | TTAGTTAATC | AAATAAATTT | ATTTTGATTT | GTTTGTTAA | TGTATTTTCT | 60 |
| CCTAGTTTAA | AGTCGATGTG | TATTTATATA | ATATTAGTAA | TATTTATTA | ACATCAATAC | 120 |
| ATGCTTCAGG | TTTTGTGTTA | GTCTTCGTTT | TTTATATGGT | TTTATCAGCG | GTGTGGTGTA | 180 |
| CGATGACGAT | TATTTAAATA | ATGACGGACT | TCTTGGTTGT | TACTTATTGA | TGTACGAAGC | 240 |
| TGAGATGTAA | CGAACCGAAC | ACATATAAAT | AACATTTTGG | ATAAGATTAC | GACTTTATTT | 300 |
| ATCGGTTGCC | ATGAAATTTG | GAAGACTTGG | GTTAAGACAC | AACCACATAT | AATGTGATGG | 360 |
| TAAATAGCAT | TTACAACTAA | TGTTAATCTT | TTGTTACAAA | TGTT | | 404 |